(12) United States Patent
Browning et al.

(10) Patent No.: US 7,947,271 B2
(45) Date of Patent: May 24, 2011

(54) METHODS OF DECREASING TUMOR VOLUME AND REDUCING TUMOR BURDEN USING TNF-RECEPTOR-COUPLING AGENTS

(75) Inventors: Jeffrey L. Browning, Brookline, MA (US); Veronique Bailly, Boxborough, MA (US); Ellen Garber, Cambridge, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

(21) Appl. No.: 12/694,092

(22) Filed: Jan. 26, 2010

(65) Prior Publication Data

US 2010/0266542 A1   Oct. 21, 2010

Related U.S. Application Data

(60) Division of application No. 11/524,786, filed on Sep. 21, 2006, now Pat. No. 7,799,902, which is a continuation of application No. PCT/US2005/009967, filed on Mar. 23, 2005.

(60) Provisional application No. 60/555,805, filed on Mar. 23, 2004.

(51) Int. Cl.
*A61K 39/00* (2006.01)
*A61K 39/395* (2006.01)

(52) U.S. Cl. ............... 424/136.1; 424/133.1; 424/135.1; 424/158.1

(58) Field of Classification Search .................. None
See application file for complete search history.

(56) References Cited

U.S. PATENT DOCUMENTS

| | | | |
|---|---|---|---|
| 4,485,045 A | 11/1984 | Regen | |
| 4,544,545 A | 10/1985 | Ryan et al. | |
| 4,816,567 A | 3/1989 | Cabilly et al. | |
| 5,082,783 A | 1/1992 | Ernst et al. | |
| 5,225,538 A | 7/1993 | Capon et al. | |
| 5,530,101 A | 6/1996 | Queen et al. | |
| 5,618,920 A | 4/1997 | Robinson et al. | |
| 5,661,004 A | 8/1997 | Browning et al. | |
| 5,670,149 A | 9/1997 | Browning et al. | |
| 5,795,964 A | 8/1998 | Browning et al. | |
| 5,859,205 A | 1/1999 | Adair et al. | |
| 5,925,351 A | 7/1999 | Browning et al. | |
| 6,072,047 A | 6/2000 | Rauch et al. | |
| 6,252,050 B1 | 6/2001 | Ashkenazi et al. | |
| 6,312,691 B1 | 11/2001 | Browning et al. | |
| 6,342,369 B1 | 1/2002 | Ashkenazi | |
| 6,403,087 B1 | 6/2002 | Browning et al. | |
| 6,417,328 B2 | 7/2002 | Alnemri | |
| 6,642,358 B1 | 11/2003 | Rauch et al. | |
| 6,669,941 B1 | 12/2003 | Browning et al. | |
| 6,743,625 B2 | 6/2004 | Ni et al. | |
| 6,872,568 B1 | 3/2005 | Ni et al. | |
| 7,001,598 B2 | 2/2006 | Browning et al. | |
| 7,030,080 B2 | 4/2006 | Browning et al. | |
| 7,060,667 B1 | 6/2006 | Browning et al. | |
| 7,662,374 B2 * | 2/2010 | Greene et al. ............... 424/130.1 |
| 2002/0004227 A1 | 1/2002 | Ashkenazi et al. | |
| 2002/0004587 A1 | 1/2002 | Miller et al. | |
| 2002/0098550 A1 | 7/2002 | Ni et al. | |
| 2002/0115154 A1 | 8/2002 | Alnemri | |
| 2002/0150985 A1 | 10/2002 | Adams et al. | |
| 2002/0155109 A1 | 10/2002 | Lynch | |
| 2002/0161195 A1 | 10/2002 | Alnemri | |
| 2002/0161196 A1 | 10/2002 | Alnemri | |
| 2002/0197254 A1 | 12/2002 | Browning et al. | |
| 2003/0133932 A1 | 7/2003 | Zhou et al. | |
| 2003/0148455 A1 | 8/2003 | Adams et al. | |
| 2003/0190687 A1 | 10/2003 | Zhou et al. | |
| 2003/0198637 A1 | 10/2003 | Zhou et al. | |
| 2003/0232049 A1 | 12/2003 | Jung | |
| 2004/0005314 A1 | 1/2004 | Escandon et al. | |
| 2004/0009552 A1 | 1/2004 | Adams et al. | |
| 2004/0058394 A1 | 3/2004 | Garber et al. | |
| 2004/0101915 A1 | 5/2004 | Deveraux et al. | |
| 2004/0136951 A1 | 7/2004 | Ni et al. | |
| 2004/0141952 A1 | 7/2004 | Ni et al. | |
| 2004/0198635 A1 | 10/2004 | Browning et al. | |
| 2004/0214235 A1 | 10/2004 | Mori et al. | |
| 2004/0228868 A1 | 11/2004 | Ashkenazi et al. | |
| 2005/0037003 A1 | 2/2005 | Browning et al. | |
| 2005/0070693 A1 | 3/2005 | Hansen et al. | |
| 2005/0079172 A1 | 4/2005 | Nasoff et al. | |
| 2005/0079184 A1 | 4/2005 | Hsing-Chang et al. | |
| 2005/0123536 A1 | 6/2005 | Law et al. | |
| 2005/0233958 A1 | 10/2005 | Ni et al. | |
| 2005/0249729 A1 | 11/2005 | Mori et al. | |
| 2005/0281811 A1 | 12/2005 | Browning et al. | |

(Continued)

FOREIGN PATENT DOCUMENTS

| | | |
|---|---|---|
| EP | 0509553 B1 | 10/1992 |
| EP | 0519596 B1 | 12/1992 |
| WO | WO-91/09967 A1 | 7/1991 |
| WO | WO-92/00329 A1 | 1/1992 |
| WO | WO-94/04679 A1 | 3/1994 |
| WO | WO-94/13808 A2 | 6/1994 |
| WO | WO-94/13808 A3 | 6/1994 |

(Continued)

OTHER PUBLICATIONS

Ichikawa K et al. Nat. Med. 7:954-961, 2001.*
Alderson, Mark R. et al., "Regulation of apoptosis and T cell activation by Fas-specific mAb," *International Immunology*, vol. 6(11):1799-1806 (1994).
Alimzhanov, Marat B. et al., "Abnormal development of secondary lymphoid tissues in lymphotoxin β-deficient mice," *Proc. Natl. Acad. Sci. USA*, vol. 94:9302-9307 (1997).
Androlewicz, Matthew J. et al., "Lymphotoxin Is Expressed as a Heteromeric Complex with a Distinct 33-kDa Glycoprotein on the surface of an Activated Human T Cell Hybridoma," *The Journal of Biological Chemistry*, vol. 267(4):2542-2547 (1992).

(Continued)

*Primary Examiner* — Robert Landsman
(74) *Attorney, Agent, or Firm* — Nelson Mullins Riley & Scarborough LLP; Megan E. Williams

(57) ABSTRACT

Receptor coupling agents, including multivalent constructs comprising anti-TNF receptor binding moieties, for treating cancer and inhibiting tumor volume in a subject are disclosed.

32 Claims, 9 Drawing Sheets

U.S. PATENT DOCUMENTS

| | | | |
|---|---|---|---|
| 2005/0282230 | A1 | 12/2005 | Ashkenazi et al. |
| 2006/0013822 | A1 | 1/2006 | Tittle et al. |
| 2006/0025576 | A1 | 2/2006 | Miller et al. |
| 2006/0035334 | A1 | 2/2006 | Adams et al. |
| 2006/0052322 | A1 | 3/2006 | Roth et al. |
| 2006/0073570 | A1 | 4/2006 | Adams et al. |
| 2006/0084147 | A1 | 4/2006 | Adams et al. |
| 2006/0088523 | A1 | 4/2006 | Andya et al. |
| 2006/0104971 | A1 | 5/2006 | Garber et al. |
| 2006/0134102 | A1 | 6/2006 | LePage et al. |
| 2006/0188498 | A1 | 8/2006 | Ashkenazi |
| 2006/0222644 | A1 | 10/2006 | Garber et al. |
| 2006/0280722 | A1 | 12/2006 | Browning et al. |
| 2007/0154476 | A1 | 7/2007 | Browning et al. |

FOREIGN PATENT DOCUMENTS

| | | |
|---|---|---|
| WO | WO-94/20625 A1 | 9/1994 |
| WO | WO-96/22788 A1 | 8/1996 |
| WO | WO-97/03687 A1 | 2/1997 |
| WO | WO-98/35986 A1 | 8/1998 |
| WO | WO-98/41629 A2 | 9/1998 |
| WO | WO-98/51793 A1 | 11/1998 |
| WO | WO-99/02653 A1 | 1/1999 |
| WO | WO-99/09165 A1 | 2/1999 |
| WO | WO-99/12963 A2 | 3/1999 |
| WO | WO-99/38525 A1 | 8/1999 |
| WO | WO-99/58679 A1 | 11/1999 |
| WO | WO-99/64461 A2 | 12/1999 |
| WO | WO-00/34335 A2 | 6/2000 |
| WO | WO-00/66156 A1 | 11/2000 |
| WO | WO-01/19861 A2 | 3/2001 |
| WO | WO-01/83560 A1 | 11/2001 |
| WO | WO-02/09755 A2 | 2/2002 |
| WO | WO-02/066516 A2 | 8/2002 |
| WO | WO-02/085946 A1 | 10/2002 |
| WO | WO-02/094880 A1 | 11/2002 |
| WO | WO-03/029420 A2 | 4/2003 |
| WO | WO-03/034984 A2 | 5/2003 |
| WO | WO-03/037913 A2 | 5/2003 |
| WO | WO-03/038043 A2 | 5/2003 |
| WO | WO-2004/001009 A2 | 12/2003 |
| WO | WO-2004/050895 A2 | 6/2004 |
| WO | WO-2004/101608 A2 | 11/2004 |
| WO | WO-2005/092383 A1 | 10/2005 |
| WO | WO-2005/100399 A2 | 10/2005 |
| WO | WO-2006/009731 A1 | 1/2006 |
| WO | WO-2006/017531 A2 | 2/2006 |
| WO | WO-2006/017859 A2 | 2/2006 |
| WO | WO-2006/017961 A1 | 2/2006 |
| WO | WO-2006/029224 A2 | 3/2006 |
| WO | WO-2006/029275 A2 | 3/2006 |
| WO | WO-2006/044908 A2 | 4/2006 |
| WO | WO-2006/083971 A2 | 8/2006 |
| WO | WO-2006/089015 A2 | 8/2006 |

OTHER PUBLICATIONS

Arulanandam, Antonio R.N. et al., "A Soluble Multimeric Recombinant CD2 Protein Identifies CD48 as a Low Affinity Ligand for Human CD2: Divergence of CD2 Ligands during the Evolution of Humans and Mice," *J. Exp. Med.*, vol. 177:1439-1450 (1993).

Baens, Mathus et al., "Construction and Evaluation of a hncDNA Library of Human 12p Transcribed Sequences Derived from a Somatic Cell Hybrid," *Genomics*, vol. 16:214-218 (1993).

Banks, Theresa A. et al., "Lymphotoxin-α-Deficient Mice," *The Journal of Immunology*, vol. 155:1685-1693 (1995).

Bernstein, David I. et al., "Effects of therapy with an immunomodulator (imiquimod, R-837) alone and with acyclovir on genital HSV-2 infection in guinea-pigs when begun after lesion development," *Antiviral Research*, vol. 20:45-55 (1993).

Bowie, James U. et al., "Deciphering the Message in Protein Sequences: Tolerance to Amino Acid Substitutions," *Science*, vol. 247:1306-1310 (1990).

Briskin, Michael J. et al., "MAdCAM-1 has homology to immunogobulin and mucin-like adhesion receptors and to IgA1," *Nature*, vol. 363:461-464 (1993).

Browning, Jeffrey L. et al., "Characterization of Surface Lymphotoxin Forms, Use of Specific Monoclonal Antibodies and Soluble Receptors," *The Journal of Immunology*, vol. 154:33-46 (1995).

Browning, Jeffrey L. et al., "Lymphotoxin and an Associated 33-kDa Glycoprotein are Expressed on the Surface of an Activated Human T Cell Hybridoma," *The Journal of Immunology*, vol. 147(4):1230-1237 (1991).

Browning, Jeffrey L. et al., "Lymphotoxin β, a Novel Member of the TNF Family That Forms a Heteromeric Complex with Lymphotoxin on the Cell Surface," *Cell*, vol. 72:847-856 (1993).

Browning, Jeffrey L. et al., "Signaling through the Lymphotoxin β Receptor Induces the Death of Some Adenocarcinoma Tumor Lines," *J. Exp. Med.*, vol. 183:867-878 (1996).

Browning, Jeffrey L. et al., "Signaling through the lymphotoxin-β receptor in conjunction with interferon-γ induces the death of A human tumor line," *The 9th International Congress of Immunology*, No. 4582 (1995).

Browning, Jeffrey L. et al., "Studies on the Differing Effects of Tumor Necrosis Factor and Lymphotoxin on the Growth of Several Human Tumor Lines," *The Journal of Immunology*, vol. 143(6):1859-1867 (1989).

Burgess, Wilson H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, vol. 111:2129-2138 (1990).

Campbell, Neil A. et al., "Methods: Monoclonal Antibody Technology," Biology, 5th Edition, Unit Seven, Animal Form and Function, Benjamin/Cummings, Laura Kennedy Ed., p. 856 (1999).

Cavert, Winston et al., "Kinetics of Response in Lymphoid Tissues to Antiretroviral Therapy of HIV-1 Infection," *Science*, vol. 276:960-964 (1997).

Chen, Chyi-Ying A. et al., "AU-rich elements: characterization and importance in mRNA degradation," *TIBS*, vol. 20:465-470 (1995).

Cher, Daniel J. et al., "Two Types of Murine Helper T Cell Clone. II. Delayed-Type Hypersensitivity is Mediated by $T_H1$ Clones," *The Journal of Immunology*, vol. 138(11):3688-3694 (1987).

Chisholm, Patricia L. et al., "Monoclonal antibodies to the integrin α-4 subunit inhibit the murine contact hypersensitivity response," *Eur. J. Immunol.*, vol. 23:682-688 (1993).

Co, Man Sung et al., "Humanized antibodies for therapy," *Nature*, vol. 351:501-502 (1991).

Colman, P.M., "Effects of amino acid sequence changes on antibody-antigen interactions," *Research in Immunology*, vol. 145:33-36 (1994).

Concha, M. et al., "Evidence for modulation of human epidermal differentiation and remodelling by CD40," British Journal of Dermatology, vol. 148:1105-1114 (2003).

Couto, Joseph R. et al., "Humanization of KC4G3, an Anti-Human Carcinoma Antibody," *Hybridoma*, vol. 13(3):215-219 (1994).

Crowe, Paul D. et al., "A Lymphotoxin-β-Specific Receptor," *Science*, vol. 264:707-710 (1994).

Crowe, Paul D. et al., "Production of lymphotoxin (LTα) and a soluble dimeric form of its receptor using the baculovirus expression system," *Journal of Immunological Methods*, vol. 168:79-89 (1994).

De Togni, Pietro et al., "Abnormal Development of Peripheral Lymphoid Organs in Mice Deficient in Lymphotoxin," *Science*, vol. 264:703-707 (1994).

Dhein, Jens et al., "Induction of Apoptosis by Monoclonal Antibody Anti-Apo-1 Class Switch Variants is Dependent on Cross-Linking of APO-1 Cell Surface Antigens," *The Journal of Immunology*, vol. 149(10):3166-3173 (1992).

Dighe, Anand S. et al., "Enhanced in Vivo Growth and Resistance to Rejection of Tumor Cells Expressing Dominant Negative IFNγ Receptors," *Immunity*, vol. 1:447-456 1994.

Dijkstra, Christine D. et al., "Marginal zone macrophage identified by a monoclonal antibody: characterization of immuno- and enzyme-histochemical properties and functional capacities," *Immunology*, vol. 55:23-30 (1985).

Düzgüneş, Nejat et al., "Liposome Targeting to HIV-Infected Cells via Recombinant Soluble CD4 and CD4-IgG (Immunoadhesin)," *Journal of Cellular Biochemistry*, p. 77, No. Q514 (1992).

Endres, Robert et al., "Mature Follicular Dendritic Cell Networks Depend on Expression of Lymphotoxin β Receptor by Radioresistant Stromal Cells and of Lymphotoxin β and Tumor Necrosis Factor by B Cells," *J. Exp. Med.*, vol. 189(1):159-167 (1999).

Eppstein, Deborah A. et al., "Biological activity of liposome-encapsulated murine interferon γ is mediated by a cell membrane receptor," *Proc. Natl. Acad. Sci. USA*, vol. 82:3688-3692 (1985).

Erickson, Sharon L. et al., "Decreased sensitivity to tumour-necrosis factor but normal T-cell cell development in TNF receptor-2-deficient mice," *Nature*, vol. 372:560-563 (1994).

Ettinger, Rachel et al., "Disrupted splenic architecture, but normal lymph node development in mice expressing a soluble lymphotoxin-β receptor-IgG1 fusion protein," *Proc. Natl. Acad. Sci. USA*, vol. 93:13102-13107 (1996).

Fägerstam, Lars G. et al., "Surface Plasmon Resonance Detection in Affinity Technologies," *Handbook of Affinity Chromatography*, Toni Kline, Ed., Marcel Dekker, Inc., Chpt. 9, pp. 229-252 (1993).

Fitch, F.W. et al., "Differential Regulation of Murine Lymphocyte Subsets," *Annu. Rev. Immunol.*, vol. 11:29-48 (1993).

Foote, Jefferson et al., "Antibody Framework Residues Affecting the Conformation of the Hypervariable Loops," *J. Mol. Biol.*, vol. 224:487-499 (1992).

Force, Walker R. et al., "Mouse Lymphotoxin-β Receptor," *The Journal of Immunology*, vol. 155:5280-5288 (1995).

Foy, Teresa M. et al., "gp39-CD40 Interactions Are Essential for Germinal Center Formation and the Development of B Cell Memory," *J. Exp. Med.*, vol. 180:157-163 (1994).

Fu, Yang-Xin et al., "B Lymphocytes Induce the Formation of Follicular Dendritic Cell Clusters in a Lymphotoxin α-dependent Fashion," *J. Exp. Med.*, vol. 187(7):1009-1018 (1998).

Fu, Yang-Xin et al., "Development and Maturation of Secondary Lymphoid Tissues," *Annu. Rev. Immunol.*, vol. 17:399-433 (1999).

Fu, Yang-Xin et al., "Lymphotoxin-α (LTα) Supports Development of Splenic Follicular Structure That Is Required for IgG Responses," *J. Exp. Med.*, vol. 185(12):2111-2120 (1997).

Fukushima, Keiko et al., "N-Linked Sugar Chain Structure of Recombinant Human Lymphotoxin Produced by CHO Cells: The Functional Role of Carbohydrate as to Its Lectin-like like Character and Clearance Velocity," *Archives of Biochemistry and Biophysics*, vol. 304(1):144-153 (1993).

Fütterer, Agnes et al., "The Lymphotoxin β Receptor Controls Organogenesis and Affinity Maturation in Peripheral Lymphoid Tissues," *Immunity*, vol. 9:59-70 (1998).

Gommerman, Jennifer L. et al., "Lymphotoxin/Light, Lymphoid Microenvironments and Autoimmune Disease," *Nature Reviews Immunology*, vol. 3:642-655 (2003).

Gonzalez, Mercedes et al., "The Sequential Role of Lymphotoxin and B Cells in the Development of Splenic Follicles," *J. Exp. Med.*, vol. 187:997-1007 (1998).

Goodwin, Raymond G. et al., "Molecular and Biological Characterization of a Ligand for CD27 Defines a New Family of Cytokines with Homology to Tumor Necrosis Factor," *Cell*, vol. 73:447-456 (1993).

Györfy, Zs. et al., "Alteration of the TNF Sensitivity and Membrane Viscosity of Target Cells," *Eur. Cytokine Netw.*, vol. 7(2):167 (1996).

Han, Shuhua et al., "Cellular Interaction in Germinal Centers, Roles of CD40 Ligand and B7-2 in Established Germinal Centers," *The Journal of Immunology*, vol. 155:556-567 (1995).

Havell, Edward A. et al., "The Antitumor Function of Tumor Necrosis Factor (TNF), I. Therapeutic Action of TNF against an Established Murine Sarcoma Is Indirect, Immunologically Dependent, and Limited by Severe Toxicity," *J. Exp. Med.*, vol. 167:1067-1085 (1988).

Heath, Sonya L. et al., "Follicular dendritic cells and human immunodeficiency virus infectivity," *Nature*, vol. 377:740-744 (1995).

Hipp, Jason D. et al., "Cancer Vaccines: An Update," In Vivo, vol. 14:571-585 (2000).

Huang, Sui et al., "Immune Response in Mice That Lack the Interferon-γ Receptor," *Science*, vol. 259:1742-1745 (1993).

Hwang, Karl J. et al., "Hepatic uptake and degradation of unilamellar sphingomyelin/cholesterol liposomes: A kinetic study," *Proc. Natl. Acad. Sci. USA*, vol. 77(7):4030-4034 (1980).

Jain, Rakesh K., "Vascular and interstitial barriers to delivery of therapeutic agents in tumors," *Cancer and Metastasis Reviews*, vol. 9:253-266 (1990).

Johne, Berit et al., "Epitope mapping and binding kinetics of monoclonal antibodies studied by real time biospecific interaction analysis using surface plasmon resonance," *Journal of Immunological Methods*, vol. 160:191-198 (1993).

Jung, Gundram et al., "Target Cell-restricted Triggering of the CD95 (APO-1/Fas) Death Receptor wtih Bispecific Antibody Fragments," *Cancer Research*, vol. 61:1846-1848 (2001).

Jurásková, Vera et al., "Interferon inducer, polyriboguanylic—polyribocytidylic acid, inhibits experimental hepatic metastases in mice," *European Journal of Pharmacology*, vol. 221:107-111 (1992).

Katz, Jonathan D. et al., "T Helper Cell Subsets in Insulin-Dependent Diabetes," *Science*, vol. 268:1185-1188 (1995).

Kawabe, Tsutomu et al., "The Immune Responses in CD40-Deficient Mice: Impaired Immunoglobulin Class Switching and Germinal Center Formation," *Immunity*, vol. 1:167-178 (1994).

Kohno, Tadahiko et al., "A second tumor necrosis factor receptor gene product can shed a naturally occurring tumor necrosis factor inhibitor," *Proc. Natl. Acad. Sci. USA*, vol. 87:8331-8335 (1990).

Kolanus, Waldemar et al., "T Cell Activation by Clustered Tyrosine Kinases," *Cell*, vol. 74:171-183 (1993).

Kolbinger, Frank et al., "Humanization of a mouse anti-human IgE antibody: a potential therapeutic for IgE-mediated allergies," *Protein Engineering*, vol. 6(8):971-980 (1993).

Kopp, William C. et al., "Immunomodulatory Effects of Interferon-γ in Patients with Metastatic Malignant Melanoma," *Journal of Immunotherapy*, vol. 13(3):181-190 (1993).

Kraal, Georg, "Cells in the Marginal Zone of the Spleen," *International Review of Cytology*, vol. 132:31-74 (1992).

Kraal, Georg et al., "Expression of the Mucosal Vascular Addressin, MAdCAM-1, on Sinus-Lining Cells in the Spleen," *American Journal of Pathology*, vol. 147(3):763-771 (1995).

Kraal, G. et al., "Lymphocyte migration in the spleen: the effect of macrophage elimination," *Immunology*, vol. 68:227-232 (1989).

Kraal, G. et al., "Marginal metallophilic cells of the mouse spleen identified by a monoclonal antibody," *Immunology*, vol. 58:665-669 (1986).

Kratz, Alexander et al., "Chronic Inflammation Caused by Lymphotoxin Is Lymphoid Neogenesis," *J. Exp. Med.*, vol. 183:1461-1472 (1996).

Kreitman, Robert J. et al., "Immunotoxins for targeted cancer therapy," *Advanced Drug Delivery Reviews*, vol. 31:53-88 (1998).

Laman, Jon D. et al., "Functions of CD40 and Its Ligand, gp39 (CD40L)," *Critical Reviews in Immunology*, vol. 16:59-108 (1996).

Lane, Peter et al., "Activated human T cells express a ligand for the human B cell-associated antigen CD40 which participates in T cell-dependent activation of B lymphocytes," *Eur. J. Immunol.*, vol. 22:2573-2578 (1992).

Langer, Robert et al., "Biocompatibility of polymeric delivery systems for macromolecules," *Journal of Biomedical Materials Research*, vol. 15:267-277 (1981).

Langer, Robert, "Controlled release of macromolecules," *Chemtech*, pp. 98-105 (1982).

Lawton, Pornsri et al., "Characterization of the Mouse Lymphotoxin-β Gene," *The Journal of Immunology*, vol. 154:239-246 (1995).

Lazar, Eliane et al., "Transforming Growth Factor α: Mutation of Aspartic Acid 47 and Leucine 48 Results in Different Biological Activities," *Molecular and Cellular Biology*, vol. 8(3):1247-1252 (1988).

Le Hir, Michel et al., "Differentiation of Follicular Dendritic Cells and Full Antibody Responses Require Tumor Necrosis Factor Receptor-1 Signaling," *J. Exp. Med.*, vol. 183:2367-2372 (1996).

Ling, Leona E. et al., "Human Type I Interferon Receptor, IFNAR, Is a Heavily Glycosylated 120-130 kD Membrane Protein," *Journal of Interferon and Cytokine Research*, vol. 15:55-61 (1995).

Loetscher, Hansruedi et al., "Recombinant 55-kDa Tumor Necrosis Factor (TNF) Receptor," *The Journal of Biological Chemistry*, vol. 266(27:18324-18329 (1991).

Mackay, Fabienne et al., "Lymphotoxin but not tumor necrosis factor functions to maintain splenic architecture and humoral responsiveness in adult mice," *Eur. J. Immunol.*, vol. 27:2033-2042 (1997).

Mackay, Fabienne et al., "Turning off follicular dendritic cells," *Nature*, vol. 395:26-27 (1998).

Maclennan, I.C.M., "2:The Structure and Function of Secondary Lymphoid Tissues," *Clinical Aspects of Immunology, Fifth Edition*, vol. 1, Blackwell Scientific Publications, P.J. Lachmann, Ed., Chpt. 2, pp. 13-30 (1993).

Maeda, Kunihiko et al., "Murine Follicular Dendritic Cells and Low Affinity Fc Receptors for IgE (FcεRII)," *The Journal of Immunology*, vol. 148(8):2340-2347 (1992).

Matsumoto, Mitsuru et al., "Affinity maturation without germinal centres in lymphotoxin-α-deficient mice," *Nature*, vol. 382:462-466 (1996).

Matsumoto, Mitsuru et al., "Distinct Roles of Lymphotoxin α and the Type I Tumor Necrosis Factor (TNF) Receptor in the Establishment of Follicular Dendritic Cells from Non-Bone Marrow-derived Cells," *J. Exp. Med.*, vol. 186(12):1997-2004 (1997).

Matsumoto, Mitsuru et al., "Lymphotoxin-α-deficient and TNF receptor-I-deficient mice define development and functional characteristics of germinal centers," *Immunological Reviews*, vol. 156:137-144 (1997).

Matsumoto, Mitsuru et al., "Role of Lymphotoxin and the Type I TNF Receptor in the Formation of Germinal Centers," *Science*, vol. 271:1289-1291 (1996).

Mendlovic, Shlomo et al., "Induction of a systemic lupus erythematosus-like disease in mice by a common human anti-DNA idiotype," *Proc. Natl. Acad. Sci. USA*, vol. 85:2260-2264 (1988).

Miller, Glenn T. et al., "Specific Interaction of Lymphocyte Function-associated Antigen 3 with CD2 Can Inhibit T Cell Responses," *J. Exp. Med.*, vol. 178:211-222 (1993).

Modlin, Robert L. et al., "Type 2 cytokines and negative immune regulation in human infections," *Current Opinion in Immunology*, vol. 5:511-517 (1993).

Mohan, Chandra et al., "Interaction Between CD40 and Its Ligand pg39 in the Development of Murine Lupus Nephritis," *The Journal of Immunology*, vol. 154:1470-1480 (1995).

Mohler, Kendall M. et al., "Soluble Tumor Necrosis Factor (TNF) Receptors Are Effective Therapeutic Agents in Lethal Endotoxemia and Function Simultaneously as Both TNF Carriers and TNF Antagonists," *The Journal of Immunology*, vol. 151(3):1548-1561 (1993).

Morrison, Sherie L. et al., "Chimeric human antibody molecules: Mouse antigen-binding domains with human constant region domains," *Proc. Natl. Acad. Sci. USA*, vol. 81:6851-6855 (1984).

Morrison, Sherie L., "In Vitro Antibodies, Strategies for Production and Application," *Ann. Rev. Immunol.*, vol. 10:239-265 (1992).

Morrissey, Philip J. et al., "CD4$^+$ T Cells That Express High Levels of CD45RB Induce Wasting Disease When Transferred into Congenic Severe Combined Immunodeficient Mice. Disease Development Is Prevented by Cotransfer of Purified CD4$^+$ T Cells," *J. Exp. Med.*, vol. 178:237-244 (1993).

Muppidi, J.R. et al., "Ligand-independent redistribution of Fas (CD95) into lipid rafts mediates clonotypic T cell death," *Nature Immunology*, vol. 5(2):182-189 (2004).

Nakache, Maurice et al., "The mucosal vascular addressin is a tissue-specific endothelial cell adhesion molecule for circulating lymphocytes," *Nature*, vol. 337:179-181 (1989).

Neumann, Brigitte et al., "Defective Peyer's Patch Organogenesis in Mice Lacking the 55-kD Receptor for Tumor Necrosis Factor," *J. Exp. Med.*, vol. 184:259-264 (1996).

Niederle, Norbert et al., "Long-Term Treatment of Chronic Myelogenous Leukemia with Different Interferons: Results from Three Studies," *Leukemia and Lymphoma*, vol. 9:111-119 (1993).

Onishi, Tetsuro et al., "A Study on Direct Antitumor Activity of Bropirimine (Oral Interferon Inducer) for Renal Cell Carcinoma," *Acta Urol. Jpn.*, vol. 40:195-200 (1994).

Paul, William E., "Immunogenicity and Antigen Structure," *Fundamental Immunology, Third Edition*, Raven Press, Chpt. 8, p. 242, Chpt. 9, pp. 292-295 (1993).

Pfeffer, Klaus et al., "Mice Deficient for the 55 kd Tumor Necrosis Factor Receptor Are Resistant to Endotoxic Shock, yet Succumb to *L. monocytogenes* Infection," *Cell*, vol. 73:457-467 (1993).

Picarella, Dominic E. et al., "Insulitis in transgenic mice expressing tumor necrosis factor β (lymphotoxin) in the pancreas," *Proc. Natl. Acad. Sci. USA*, vol. 89:10036-10040 (1992).

Picker, Louis J. et al., "Physiological and Molecular Mechanisms of Lymphocyte Homing," *Annu. Rev. Immunol.*, vol. 10:561-591 (1992).

Pleskov, V.M. et al., "The receptor-mediated endocytosis of influenza viruses and low-density density lipoproteins by tissue cells," *Vopr. Virusol.*, vol. 39(3):121-125 (1994).

Powell, Kenneth L. et al., "The antiviral effects of nitric oxide," *Trends in Microbiology*, vol. 3(3):81-88 (1995).

Powrie, Fiona et al., "Inhibition of Th1 Responses Prevents Inflammatory Bowel Disease in *scid* Mice Reconstituted with CD45RB$^{hi}$ CD4$^+$ T Cells," *Immunity*, vol. 1:553-562 (1994).

Powrie, Fiona et al., "Phenotypically distinct subsets of CD4$^+$ T cells induce or protect from chronic intestinal inflammation in C. B-17 *scid* mice," *International Immunity*, vol. 5(11):1461-1471 (1993).

Queen, Cary et al., "A humanized antibody that binds to the interleukin 2 receptor," *Proc. Natl. Acad. Sci. USA*, vol. 86:10029-10033 (1989).

Raitano, Arthur B. et al., "Tumor Necrosis Factor Up-regulates γ-Interferon Binding in a Human Carcinoma Cell Line," *The Journal of Biological Chemistry*, vol. 265(18):10466-10472 (1990).

Reed, Steven G. et al., "T-cell and cytokine responses in leishmaniasis," *Current Opinion in Immunobiology*, vol. 5:524-531 (1993).

Rennert, Paul D. et al., "Surface Lymphotoxin α/β Complex Is Required for the Development of Peripheral Lymphoid Organs," *J. Exp. Med.*, vol. 184:1999-2006 (1996).

Rennert, P.D. et al., "Normal Development of Lymph Nodes is Disrupted by Soluble LT beta Receptor—Ig Fusion Protein," *Eur. Cytokine Netw.*, vol. 7(2):167 (1996).

Renshaw, Blair R. et al., "Humoral Immune Responses in CD40 Ligand-deficient Mice," *J. Exp. Med.*, vol. 1994:1889-1900 (1994).

Reutershealth.com, "What is Systemic Erythematosus?" retrieved online at http://www.reutershealth.com/wellconnected/doc/63.html (2004).

Riechmann, Lutz et al., "Reshaping human antibodies for therapy," *Nature*, vol. 332:323-327 (1988).

Roitt, Ivan M. et al., Immunology, Third Edition, Mosby, Chpt. 1, pp. 1.1-1.12, Chpts. 19-22, pp. 19.1-22.12 (1993).

Romagnani, Sergio, "Lymphokine Production by Human T Cells in Disease States," *Annu. Rev. Immunol.*, vol. 12:227-257 (1994).

Rothe, Joachim et al., "Mice lacking the tumour necrosis factor receptor 1 are resistant to TNF-mediated toxicity but highly susceptible to infection by *Listeria monocytogenes*," *Nature*, vol. 364:798-802 (1993).

Ruddle, Nancy H. et al, "An Antibody to Lymphotoxin and Tumor Necrosis Factor Prevents Transfer of Experimental Allergic Encephalomyelitis," *J. Med. Med.*, vol. 172:1193-1200 (1990).

Rudikoff, Stuart et al., "Single amino acid substitution altering antigen-binding specificity," *Proc. Natl. Acad. Sci. USA*, vol. 79:1979-1983 (1982).

Sayegh, Mohamed H. et al., "CD28-B7 Blockade after Alloantigenic Challenge In Vivo Inhibits Th1 Cytokines but Spares Th2," *J. Exp. Med.*, vol. 181:1869-1874 (1995).

Schiller, Joan H. et al., "Biological and Clinical Effects of Intravenous Tumor Necrosis Factor-α Administered Three Times Weekly," *Cancer Research*, vol. 51:1651-1658 (1991).

Schoenfeld, Hans-Joachim et al., "Efficient Purification of Recombinant Human Tumor Necrosis Factor β from *Escherichia coli* Yields Biologically Active Protein with a Trimeric Structure That Binds to Both Tumor Necrosis Factor Receptors," *The Journal of Biological Chemistry*, vol. 266(6):3863-3869 (1991).

Schriever, Folke et al., "The Central Role of Follicular Dendritic Cells in Lymphoid Tissues," *Advances in Immunology*, vol. 51:243-284 (1992).

Selmaj, Krzysztof et al., "Identification of Lymphotoxin and Tumor Necrosis Factor in Multiple Sclerosis Lesions," *J. Clin. Invest.*, vol. 87:949-954 (1991).

Sidman, Kenneth R. et al., "Controlled Release of Macromolecules and Pharmaceuticals from Synthetic Polypeptides Based on Glutamic Acid," *Biopolymers*, vol. 22:547-556 (1983).

Slepushkin, A.N. et al., "A comparative study of live and inactivated influenza vaccines: the organization of the observation and the results of a study of their reactogenicity and immunogenicity," *Vopr. Virusol.*, vol. 39(3):129-131 (1994).

Smith, Craig A. et al., "A Receptor for Tumor Necrosis Factor Defines an Unusual Family of Cellular and Viral Proteins," *Science*, vol. 248:1019-1023 (1990).

Smith, Craig A. et al., "The TNF Receptor Superfamily of Cellular and Viral Proteins: Activation, Costimulation, and Death," *Cell*, vol. 78:959-962 (1994).

Smolen, Josef S., "Therapy of systemic lupus erythematosus: a look into the future," *Arthritis Res.*, vol. 4(Suppl. 3):S25-S30 (2002).

Tartaglia, Louis A. et al., "Two TNF receptors," *Immunology Today*, vol. 13(5):151-153 (1992).

Tempest, Philip R. et al., "Reshaping a Human Monoclonal Antibody to Inhibit Human Respiratory Syncytial Virus Infection In Vivo," *Bio/Technology*, vol. 9:266-271 (1991).

Tew, John G. et al., "Follicular Dendritic Cells as Accessory Cells," *Immunological Reviews*, vol. 117:185-211 (1990).

Tibbetts, Randal S. et al., "Cardiac Antigen-Specific Autoantibody Production is Associated with Cardiomyopathy in *Trypanosoma cruzi*-Infected Mice," *Journal of Immunology*, vol. 152:1493-1499 (1994).

Toellner, Kai-Michael et al., "Immunoglobulin Switch Transcript Production In Vivo Related to the Site and Time of Antigen-specific B Cell Activation," *J. Exp. Med.*, vol. 183:2303-2312 (1996).

Traunecker, André et al., "Highly efficient neutralization of HIV with recombinant CD4-immunoglobulin molecules," *Nature*, vol. 339:68-70 (1989).

Trethewey, Pat, "Systemic Lupus Erythematosus," *Dimens. Crit. Care Nurs.*, vol. 23(3):111-115 (2004).

Ullrich, Axel et al., "Signal Transduction by Receptors with Tyrosine Kinase Activity," *Cell*, vol. 61:203-212 (1990).

Van Dullemen, Hendrik M. et al., "Treatment of Crohn's Disease With Anti-Tumor Necrosis Factor Chimeric Monoclonal Antibody (cA2)," *Gastroenterology*, vol. 109:129-135 (1995).

Van Kooten, Cees et al., "CD40-CD40 Ligand: A Multifunctional Receptor—Ligand Pair," *Advances in Immunology*, vol. 61:1-77 (1996).

Van Vliet, Els et al., "Reticular Fibroblasts in Peripheral Lymphoid Organs Identified by a Monoclonal Antibody," *The Journal of Histochemistry and Cytochemistry*, vol. 34(7):883-890 (1986).

Ware, C.F. et al., "The Ligands and Receptors of the Lymphotoxin System," *Pathways for Cytolysis, Current Topics Microbiol. Immunol.*, pp. 175-218 (1995).

Winter, Greg et al., "Man-made antibodies," *Nature*, vol. 349:293-299 (1991).

Wu, Qiang et al., "The Requirement of Membrane Lymphotoxin for the Presence of Dendritic Cells in Lymphoid Tissues," *J. Exp. Med.*, vol. 190(5):629-638 (1999).

Xu, Jianchao et al., "Mice Deficient for the CD40 Ligand," *Immunity*, vol. 1:423-431 (1994).

Yonehara, Shin et al., "A Cell-killing Monoclonal Antibody (Anti-Fas) to a Cell Surface Antigen Co-downregulated with the Receptor of Tumor Necrosis Factor," *J. Exp. Med.*, vol. 169:1747-1756(1989).

Zhou, M. et al., "Real-Time Measurements of Kinetics of EGF Binding to Soluble EGF Receptor Monomers and Dimers Support the Dimerization Model for Receptor Activation," *Biochemistry*, vol. 32:8193-8198 (1993).

International Search Report for Application No. PCT/US97/19436, dated May 28, 1998.

International Search Report and Written Opinion for Application No. PCT/US2005/009967, dated Aug. 3, 2005.

International Preliminary Report on Patentability for Application No. PCT/US2005/009967, dated Sep. 26, 2006.

* cited by examiner

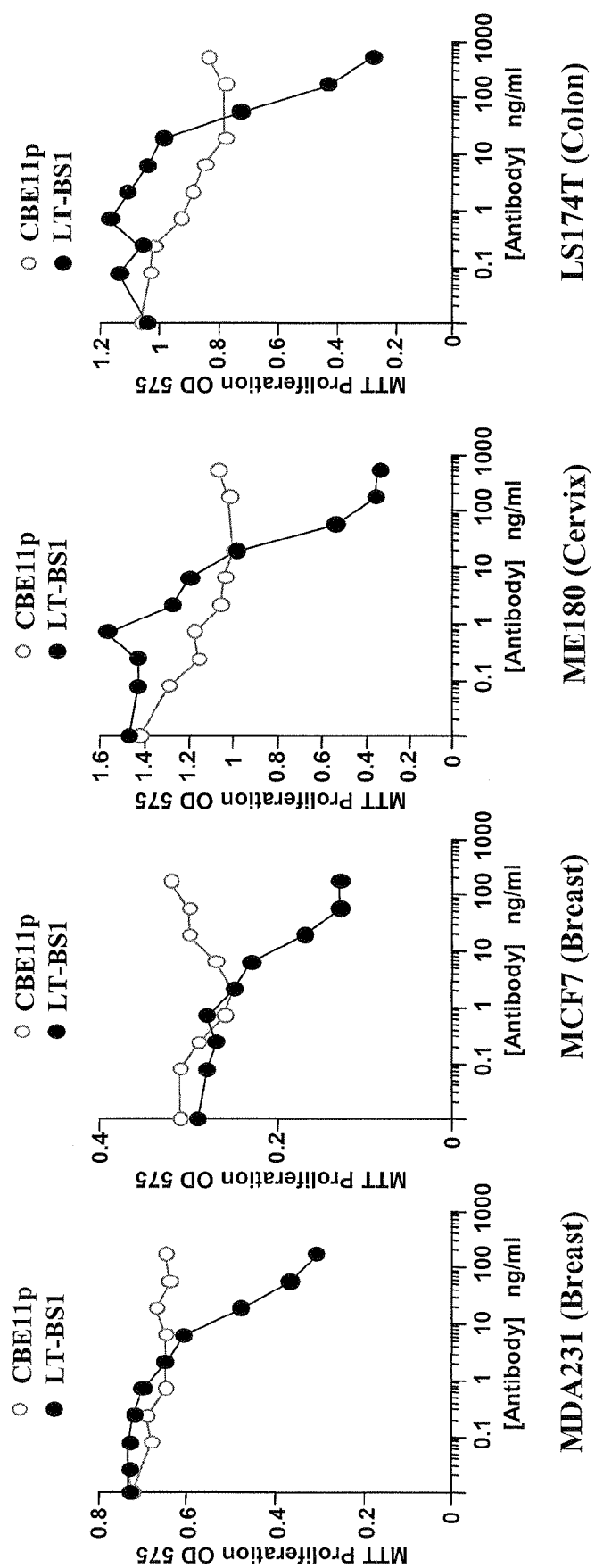

TRAIL-R/LTBR Bispecific 1 (LT-BS1)

METHODS OF DECREASING TUMOR VOLUME AND REDUCING TUMOR BURDEN USING TNF-RECEPTOR-COUPLING AGENTS

RELATED APPLICATIONS

This application is a divisional of U.S. patent application Ser. No. 11/524,786 filed on Sep. 21, 2006, now U.S. Pat. No. 7,799,902, which is a continuation of International Patent Application Serial No. PCT/US2005/009967, filed on Mar. 23, 2005, which claims priority to U.S. Provisional Application No. 60/555,805, filed Mar. 23, 2004, now expired. The entire contents of each of these patents and patent applications are hereby incorporated herein by reference.

BACKGROUND OF THE INVENTION

The ability to induce cell death by various members of the TNF family has been pursued by oncologists for almost 20 years. Originally, TNF itself was used to treat solid tumors and eventually was found to be applicable to the local treatment of melanoma by whole limb perfusion (Lejeune et al. (1998) Curr Opin Immunol 10:573)) Most recently, activation of TNF receptors by ligands or anti-receptor antibodies has sparked clinical interest. Activation of the Fas receptor, for example, has shown considerable promise, although it may be limited by liver toxicity. Activation of TRAILR1 or TRAILR2 by the TRAIL ligand, another member of the TNF family, has been reported to transduce an apoptotic signal to TRAIL-sensitive cancer cells (Griffith et al., J. Immunol. 162:2597, 1999; and Degli-Esposti et al., Immunity, 7:813-820, 1997). Activation of LT-β-R, yet another member of the TNF family, by soluble ligands or agonistic antireceptor monoclonal antibodies has also been shown to induce the death of certain carcinomas (Lawerence et al., (2001) Nat Med 7:383, Ichikawa et al., (2001) Nat Med 7:954). Treatment with agonist TNF activating agents would thus be useful for treating or reducing the advancement, severity or effects of neoplasia in subjects (e.g., humans).

SUMMARY OF THE INVENTION

The invention describes a receptor coupling agent which specifically activates at least two distinct TNF family receptors. In one embodiment, the receptor coupling agent enhances receptor signaling. In another embodiment, the receptor coupling agent induces formation of heteromeric receptor complexes. In one embodiment, the receptor coupling agent comprises a first binding specificity for one receptor and a second binding specificity for the other receptor. In one embodiment, the first binding specificity is conferred or effected by an antibody or antigen binding fragment thereof. In another embodiment, the second binding specificity is conferred or effected by an antibody or antigen binding fragment thereof. The binding specificity can be conferred, for example, by a single chain Fv fragment. In another embodiment, the first binding specificity is effected by a natural ligand for the receptor, and the second binding specificity is derived from an antibody or antigen binding fragment thereof. In still another embodiment, the first binding specificity is conferred by a natural ligand for the receptor, and the second binding specificity is conferred by a natural ligand for the receptor.

The invention describes a receptor coupling agent which specifically activates at least two distinct TNF family receptors, wherein at least one receptor contains a death domain. In one embodiment, the receptor coupling agent enhances receptor signaling or induces formation of heteromeric receptor complexes, wherein at least one receptor contains a death domain. In one embodiment, the receptor containing a death domain is selected from the group consisting of TNFR1 (DR1), Fas (DR2), TRAIL-R1 (DR4), TRAIL-R2 (DR5), DR6 and p75NGF-R.

The invention includes a receptor coupling agent which activates at least two distinct TNF family receptors, wherein at least one receptor does not contain a death domain. The invention also describes a receptor coupling agent which enhances receptor signaling or induces formation of heteromeric receptor complexes, wherein at least one receptor does not contain a death domain. In one embodiment, the receptor does not contain a death domain and is involved in tissue differentiation. In another embodiment, the receptor which does not contain a death domain is selected from the group consisting of LTBR, RANK, EDAR1, XEDAR, Fn14, Troy/Trade, and TAJ.

The invention also describes a receptor coupling agent which specifically activates at least two distinct TNF family receptors, wherein at least one receptor is involved in tissue differentiation. The invention also describes a receptor coupling agent which enhances receptor signaling or induces formation of heteromeric receptor complexes, wherein at least one receptor is involved in tissue differentiation. In one embodiment, the receptor is selected from the group consisting of LTBR, RANK, EDAR1, XEDAR, Fn14, Troy/Trade/TAJ, and p75NGF-R.

In one embodiment, the receptor coupling agent activates a non-death domain containing TNF receptor and a death domain containing receptor, e.g., LTBR/TRAIL-R1; LTBR/TRAIL-R2; LTBR/p75NGF-R; Fn14/p75NGF-R; and p75NGF-R/TAJ.

In another embodiment, the receptor coupling agent activates at least two TNF receptors which do not contain death domains, e.g., LTBR/Fn14; LTBR/RANK; Fn14/TAJ; LTBR/EDAR; LTBR/XEDAR; RANK/EDAR; RANK/XEDAR; and TAJ/EDAR; and TAJ/XEDAR.

In still another embodiment of the invention, the receptor coupling agent activates at least two death domain containing receptors.

In addition, the invention describes a receptor coupling agent which specifically activates at least two distinct TNF family receptors, wherein at least one receptor is involved in immune regulation. In one embodiment, the receptor is selected from the group consisting of TNFRII, HVEM, CD27, CD30, CD40, 4-1BB, OX40, GITR, TACI, BAFF-R, BCMA, and RELT.

The invention provides a receptor coupling agent which specifically activates at least two distinct TNF family receptors, wherein at least one of the receptors is not overexpressed on normal liver or endothelial cells.

The invention also describes a receptor coupling agent which specifically activates at least two distinct TNF family receptors, wherein the receptor coupling agent comprises a first binding specificity for one receptor and a second binding specificity for the other receptor. In one embodiment, the receptor coupling agent enhances receptor signaling or induces formation of heteromeric receptor complexes. In one embodiment, the first binding specificity is conferred by or derived from an anti-LTβ receptor (LTβR) antibody, or antigen binding fragment thereof. An example of an anti-LTβR antibody includes a humanized CBE11 antibody. In one embodiment, the second binding specificity is conferred by or derived from an anti-TRAIL-R2 antibody, or antigen binding fragment thereof. Examples of the anti-TRAIL-R2 antibody are a humanized or a chimeric 14A2 antibody. In another embodiment, the first binding specificity is conferred by a single chain Fv fragment of a humanized CBE11 antibody and the second binding specificity is conferred by a 14A2 antibody.

The invention describes a receptor coupling agent which specifically activates at least two distinct TNF family receptors, wherein the receptor coupling agent comprises a first binding specificity for one receptor and a second binding specificity for the other receptor, wherein the first binding specificity comprises at least two trimeric ligand-Fc constructs that are commonly formed from three dimeric Fc domains and six ligand molecules. In this case, the second binding specificity would comprise from the three antibody molecules.

The invention describes a receptor coupling agent which specifically activates at least two distinct TNF family receptors, wherein at least one of the TNF family receptors is not normally found in a raft environment on the cell surface. In one embodiment, the receptor coupling agent enhances receptor signaling or induces formation of heteromeric receptor complexes, wherein at least one of the TNF family receptors is not normally found in a raft environment on the cell surface.

The invention includes a receptor coupling agent which specifically activates at least two distinct TNF family receptors, enhances receptor signaling or induces formation of heteromeric receptor complexes, wherein at least one of the TNF family receptors is normally found in a raft environment on the cell surface.

The invention further describes a receptor coupling agent which specifically activates at least two distinct TNF family receptors or enhances receptor signaling, wherein the signal strength is enhanced through the receptors.

The invention includes a receptor coupling agent comprising at least two antibodies or antigen binding fragments thereof, wherein each antibody binds a distinct TNF family receptor, thereby inducing formation of a heteromeric receptor complex. In one embodiment, the antibody is derived from an anti-LTβR antibody, including, for example, a humanized CBE11 antibody. In another embodiment, the second antibody is derived from an anti-TRAIL-R2 antibody, including, for example, a humanized or chimeric 14A2 antibody.

In one embodiment, the invention includes a method for localizing a TNF family receptor to a cell membrane raft comprising administering a receptor coupling agent comprising a first binding specificity for a rafted TNF family receptor and a second binding specificity for a non-rafted TNF family receptor, wherein binding of the receptor coupling agent localizes the non-rafted TNF receptor to a raft in the cell membrane.

The invention also includes a method for enhancing receptor signaling comprising administering a receptor coupling agent which specifically activates at least two distinct TNF family receptors, enhances receptor signaling and induces formation of heteromeric receptor complexes.

In still another embodiment, the invention describes a method of decreasing tumor volume comprising administering to a subject a receptor coupling agent which specifically activates at least two distinct TNF family receptors, enhances receptor signaling, or induces formation of heteromeric receptor complexes.

In still another embodiment, the invention includes a method of treating cancer comprising administering to a subject a receptor coupling agent which specifically activates at least two distinct TNF family receptors, enhances receptor signaling, or induces formation of heteromeric receptor complexes. In one embodiment, the receptor coupling agent is administered in the presence of IFNγ. In another embodiment, the receptor coupling agent is administered in the presence of a chemotherapeutic agent.

The invention also comprises a receptor coupling agent which activates at least two distinct TNF family receptors and induces formation of a heteromeric receptor complex comprising a first binding specificity directed to a first TNF receptor and a second binding specificity directed to a second TNF receptor. In one embodiment, the first and second binding specificities are directed to TNF receptors, including a non-death domain containing TNF receptor and a death domain containing TNF receptor; two non-death domain containing TNF receptors; or two death domain containing TNF receptors. In another embodiment, at least one binding specificity is directed to a non-death domain containing TNF receptor associated with tissue differentiation. In still another embodiment, two non-death domain containing TNF receptors are selected from the group consisting of LTBR/Fn14; LTBR/RANK; Fn14/TAJ; LTBR/EDAR; LTBR/XEDAR; RANK/EDAR; RANK/XEDAR; TAJ/EDAR; and TAJ/XEDAR. In another embodiment of the invention, the non-death domain containing TNF receptor and the death domain containing TNF receptor is selected from the group consisting of LTBR/TRAIL-R1; LTBR/TRAIL-R2; LTBR/p75NGF-R; Fn14/p75NGF-R; and p75NGF-R/TAJ.

BRIEF DESCRIPTION OF THE DRAWINGS

FIGS. 8a-d graphically depict results from a 4-day MTT growth assay with 80 U/ml of IFNγ in a range of tumor cell types, including breast, cervical, and colon. The results show the effects of receptor coupling agent LT-BS1 and pentameric CBE11 antibody at inhibiting various types of carcinoma cell growth, including breast (A, B), cervical (C), and colon (D).

DETAILED DESCRIPTION OF THE INVENTION

I. Definitions

Figure 1B:
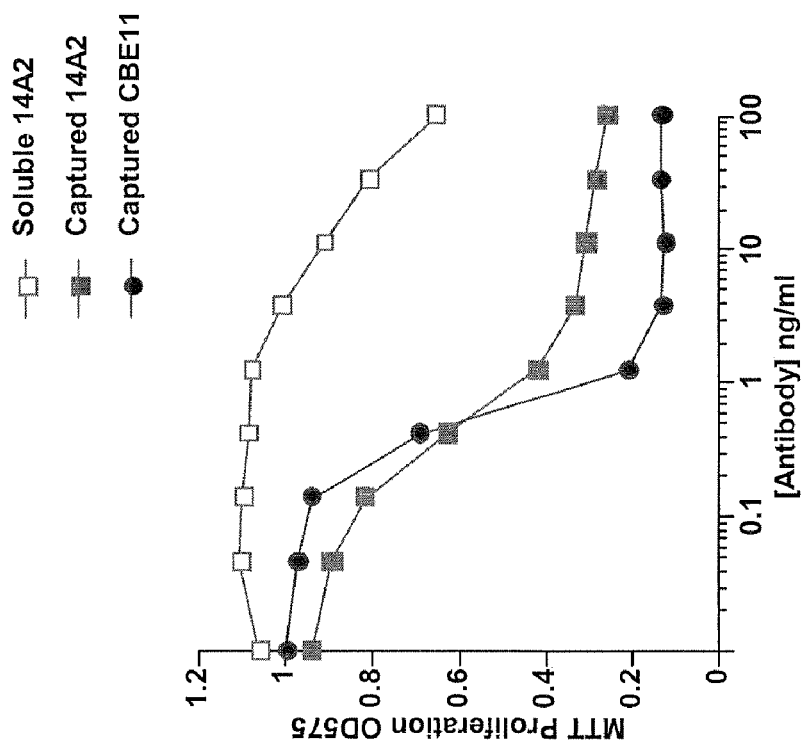
FIGS. 1a-b graphically depict results from a WiDr cell 4 day proliferation assay. Results show that anti-TRAIL-R2 antibody, 14A2, and anti-LTβR antibody, CBE11, were both able to induce WiDr death through agonist activity.

For convenience, before further description of the present invention, certain terms employed in the specification, examples and appended claims are defined here.

The term "administering" includes any method of delivery of a compound of the present invention, including but not limited to, a pharmaceutical composition or therapeutic agent, into a subject's system or to a particular region in or on a subject. The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration. "Parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

As used herein, the term "antibody" is meant to refer to complete, intact antibodies, as well as Fab, Fab', F(ab)$_2$, F$_v$, and other fragments thereof that impart desired binding specificities to the constructs of the instant invention. Antibodies include, for example, monoclonal antibodies such as murine monoclonal antibodies, chimeric antibodies, anti-idiotypic antibodies, anti-anti-idiotypic antibodies, and humanized antibodies, as well as mutivalent forms thereof. The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. "Constant" domains on the light chain are referred to interchangeably as "light chain constant regions", "light chain constant domains", "CL" regions or "CL" domains). "Constant" domains on the heavy chain are referred to interchangeably as "heavy chain constant regions", "heavy chain constant domains", "CH" regions or "CH" domains). "Variable" domains on the light chain are referred to interchangeably as "light chain variable regions", "light chain variable domains", "VL" regions or "VL" domains). "Variable" domains on the heavy chain are referred to interchangeably as "heavy chain constant regions", "heavy chain constant domains", "CH" regions or "CH" domains).

The term "region" refers to a part or portion of an antibody chain and includes constant or variable domains as defined herein, as well as more discrete parts or portions of said domains. For example, light chain variable domains or regions include "complementarity determining regions" or "CDRs" interspersed among "framework regions" or "FRs", as defined herein.

Immunoglobulins or antibodies can exist in monomeric or polymeric form. The term "antigen-binding fragment" refers to a polypeptide fragment of an immunoglobulin or antibody binds antigen or competes with intact antibody (i.e., with the intact antibody from which they were derived) for antigen binding (i.e., specific binding). The term "conformation" refers to the tertiary structure of a protein or polypeptide (e.g., an antibody, antibody chain, domain or region thereof). For example, the phrase "light (or heavy) chain conformation" refers to the tertiary structure of a light (or heavy) chain variable region, and the phrase "antibody conformation" or "antibody fragment conformation" refers to the tertiary structure of an antibody or fragment thereof. Binding fragments are produced by recombinant DNA techniques, or by enzymatic or chemical cleavage of intact immunoglobulins. Binding fragments include Fab, Fab', F(ab')$_2$, Fabc, Fv, single chains, and single-chain antibodies. Other than "bispecific" or "bifunctional" immunoglobulins or antibodies, an immunoglobulin or antibody is understood to have each of its binding sites identical. A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, (1990) *Clin. Exp. Immunol.* 79:315-321; Kostelny et al., (1992) *J. Immunol.* 148, 1547-1553.

The term "antibody construct" refers to a recombinant molecule that comprises two or more antigen-binding fragments coming from the variable domains of the heavy chain and light chain of an antibody. An antibody construct may comprise the entire or part of the constant regions of an antibody from any of the five Ig classes (for example IgA, IgD, IgE, IgG and IgM). For example, the antibody construct may be made of an antibody which heavy chains comprise at their C-terminus a single chain variable fragment. In another example, the antibody construct may be made of the entire or part of the constant region of the two heavy chains of an antibody which comprise at their carboxy- and amino-termini a single chain variable fragment. An example of antibody constructs that impart the desired binding specificities is depicted schematically in FIG. 9. In yet another example, the antibody construct may comprise two heavy chains having two or more variable regions and two light chains having one or more variable regions where the two heavy chains are joined by a disulfide bond or other covalent linkage. In another example, the antibody construct may comprise two heavy chains comprising two or more variable regions where the two heavy chains are joined by a disulfide bond or other covalent linkage.

The term "antigen" as used herein, means a molecule which is reactive with a specific antibody.

The term "antigen binding site" or "antigen recognition site" refers to a region of an antibody that specifically binds an epitope on an antigen.

The term "apoptosis", "apoptotic cell death" or "programmed cell death" as used herein refers to any cell death that results from the cascade of cellular events that occur at specific stages of cellular differentiation and in response to specific stimuli.

Apoptotic cell death is often characterized by condensation of the cytoplasm and nucleus of dying cells.

The term "binding specificity" is a property of the disclosed receptor coupling agents that is conferred, imparted, effected or derived from a binding moiety which is directed to a specific TNF family receptor. A binding specificity of the invention may be conferred by binding moieties that include, for example, an antibody, or antigen binding fragment thereof, a single chain Fv fragment soluble ligands, fc fusions or the like. Those skilled in the art will appreciate that, for the purposes of the instant application, the terms "binding specificity" and "binding moiety" may be used interchangeably unless otherwise dictated by contextual restraints. Thus, a binding specificity (binding moiety) may also include a TNF ligand which interacts with a TNF family receptor. In one embodiment of the invention, a receptor coupling agent comprises at least one binding specificity (or binding moiety) for one TNF receptor, and a second binding specificity (or binding moiety) for another TNF receptor.

The term "cancer" or "neoplasia" refers in general to any malignant neoplasm or spontaneous growth or proliferation of cells. The term as used herein encompasses both fully developed malignant neoplasms, as well as premalignant lesions. A subject having "cancer", for example, may have a tumor or a white blood cell proliferation such as leukemia. In certain embodiments, a subject having cancer is a subject having a tumor, such as a solid tumor. Cancers involving a solid tumor include but are not limited to non small cell lung cancer (NSCLC), testicular cancer, lung cancer, ovarian cancer, uterine cancer, cervical cancer, pancreatic cancer, colorectal cancer (CRC), breast cancer, as well as on prostate, gastric, skin, stomach, esophagus and bladder cancer.

The term "chemotherapeutic agent" refers to any small molecule or biologic used to treat disease caused by a foreign cell or malignant cell, such as a tumor cell. Non-limiting examples of chemotherapeutic agents include agents that disrupt DNA synthesis, are inhibitors of topoisomerase I, are alkylating agents, or are plant alkaloids. Exemplary biologic chemotherapeutic agents comprise rituximab, ibritumomab, bevacizumab and trastuzumab. Those skilled in the art will appreciate that other chemotherapeutic agents compatible with the teachings of the instant application are readily discernable.

The term "agent that disrupts DNA synthesis" refers to any molecule or compound able to reduce or inhibit the process of DNA synthesis. Examples of agents that disrupt DNA synthesis include but are not limited to nucleoside analogs such as pyrimidine or purine analogs, including, for example but not limited to, gemcitabine or alternatively anthracycline compounds, including for example but not limited to, adriamycin, daunombicin, doxorubicin, and idambicin and epipodophyllotoxins such as etoposide and teniposide. The term "topoisomerase I inhibitor" refers to a molecule or compound that inhibits or reduces the biological activity of a topoisomerase I enzyme. Including for example, but not limited to, camptosar. The term "alkylating agent" refers to any molecule or compound able to react with the nucleophilic groups of (for examples, amines, alcohols, phenols, organic and inorganic acids) and thus add alkyl groups (for example, ethyl or methyl groups) to another molecule such as a protein or nucleic acid. Examples of alkylating agents used as chemotherapeutic agents include bisulfan, chlorambucil, cyclophosphamide, ifosfamide, mechlorethamine, melphalan, thiotepa, various nitrosourea compounds, and platinum compounds such as cisplatin and carboplatin. The term "plant alkaloid" refers a compound belonging to a family of alkaline, nitrogen-containing molecules derived from plants that are biologically active and cytotoxic. Examples of plant alkoids include, but are not limited to, taxanes such as taxol, docetaxel and paclitaxel and vincas such as vinblastine, vincristine, and vinorelbine.

The term "chimeric antibody" refers to an antibody whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as IgG1 and IgG4. Human isotype IgG1 is preferred. A typical chimeric antibody is thus a hybrid protein consisting of the V or antigen-binding domain from a mouse antibody and the C or effector domain from a human antibody.

The term "death domain" refers to a cytoplasmic region of a TNF family receptor which is involved TNF-mediated cell death signaling and cell-cytotoxicity induction mediated by these receptors. This region couples the receptor to caspase activation via adaptor proteins resulting in activation of the extrinsic death pathway. Examples of TNF receptors which contain death domains include, but are not limited to, TNFR1 (DR1), Fas (DR2), TRAIL-R1 (DR4), TRAIL-R2 (DR5), p75NGFR, and DR6.

The term "effective amount" refers to that amount of a compound, material, or composition comprising a compound of the present invention which is sufficient to effect a desired result, including, but not limited to, for example, reducing tumor volume either in vitro or in vivo. An effective amount of a pharmaceutical composition of the present invention is an amount of the pharmaceutical composition that is sufficient to effect a desired clinical result, including but not limited to, for example, ameliorating, stabilizing, preventing or delaying the development of cancer in a patient. In either case, an effective amount of the compounds of the present invention can be administered in one or more administrations. Detection and measurement of these above indicators are known to those of skill in the art, including, but not limited for example, reduction in tumor burden, inhibition of tumor size, reduction in proliferation of secondary tumors, expression of genes in tumor tissue, presence of biomarkers, lymph node involvement, histologic grade, and nuclear grade.

The term "epitope" refers to the region of an antigen to which an antibody or antibody construct binds preferentially and specifically. A monoclonal antibody binds preferentially to a single specific epitope of a molecule that can be molecularly defined. In the present invention, multiple epitopes can be recognized by a multispecific antibody.

The term "Fv fragment" refers to the fragment of an antibody comprising the variable domains of its heavy chain and light chain. The term Fc fragment refers to the fragment of an antibody comprising the constant domain of its heavy chain.

The term "humanized immunoglobulin" or "humanized antibody" refers to an immunoglobulin or antibody that includes at least one humanized immunoglobulin or antibody chain (i.e., at least one humanized light or heavy chain). The term "humanized immunoglobulin chain" or "humanized antibody chain" (i.e., a "humanized immunoglobulin light chain" or "humanized immunoglobulin heavy chain") refers to an immunoglobulin or antibody chain (i.e., a light or heavy chain, respectively) having a variable region that includes a variable framework region substantially from a human immunoglobulin or antibody and complementarity determining regions (CDRs) (e.g., at least one CDR, preferably two CDRs, more preferably three CDRs) substantially from a non-human immunoglobulin or antibody, and further includes constant regions (e.g., at least one constant region or portion thereof, in the case of a light chain, and preferably three constant regions in the case of a heavy chain). The term "humanized variable region" (e.g., "humanized light chain variable region" or "humanized heavy chain variable region") refers to a variable region that includes a variable framework region substantially from a human immunoglobulin or antibody and complementarity determining regions (CDRs) substantially from a non-human immunoglobulin or antibody.

The term "heteromeric receptor complex" refers to a complex comprising a receptor coupling agent and two or more receptor(s) to which the receptor coupling agent is targeted. In one embodiment, the heteromeric receptor complex of the invention comprises a receptor coupling agent and at least two TNF family receptors which the agent is targeted to activate. Preferably, signaling through the receptors is enhanced as a result of formation of the heteromeric receptor complex. In one embodiment of the invention, the heteromeric receptor complex forms on a lipid raft in the cell membrane. In another embodiment, the heteromeric receptor complex of the invention forms outside of a lipid raft on the cell membrane.

The term "inhibition of tumor volume" refers to any decrease or reduction in a tumor volume.

The term "ligand" refers to any molecule which binds to a specific site on a protein or other molecule. A ligand is often a polypeptide or a compound that binds to a receptor protein in a high affinity and specific manner to elicit a functional response. For example ligands of the invention include TNF family receptor ligands. The term "natural ligand" refers to a ligand which binds to a receptor under normal physiological conditions. The term "receptor" refers herein to a structure, usually a polypeptide, located on or in a cell, which recognizes a binding molecule, i.e., a ligand, and thereby induces a cellular response. Receptors of the invention include TNF family receptors, including, for example, TRAIL-R2, HVEM, and LTβR.

The term "TNF family receptor" or "TNF-R" refers to receptors which belong to the TNF receptor superfamily characterized by disulfide bonds which form "cysteine-rich domains" or CRDs. TNF receptor family members generally consist of an extracellular domain, a transmembrane domain and an intracellular signaling domain (see Locksley et al. (2001) Cell 104:487 for review). The extracellular domain is built from 1 to 6 copies of a tightly disulphide-bonded domain and is recognized on the basis of the unique arrangement of cysteine residues (Banner et al. (1993) Cell 73:431). Each TNF receptor binds to a corresponding ligand, although one ligand may share several receptors.

The term "lymphotoxin-beta receptor (LTβR) agonist" refers to any agent which can augment ligand binding to LTβR, cell surface LTβR clustering and/or LTβR signaling.

Figure 9:
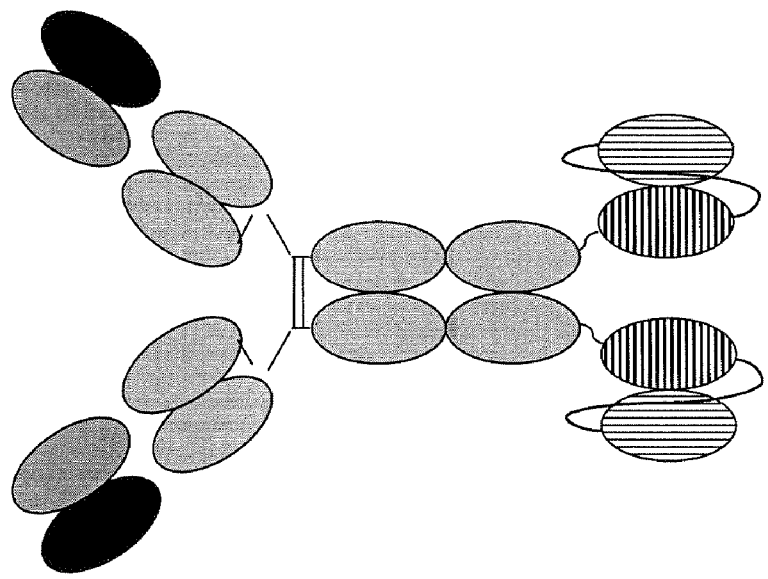
FIG. 9 depicts a schematic drawing of the receptor coupling agent LT-BS1 construct comprising anti-TRAIL-R2 antibody 14A2 and LTβR scFv antibody CBE11 (striped).

The phrase "multivalent antibody" or "multivalent antibody construct" refers to an antibody or antibody construct comprising more than one antigen recognition site. For example, a "bivalent" antibody construct has two antigen recognition sites, whereas a "tetravalent" antibody construct has four antigen recognition sites. The terms "monospecific", "bispecific", "trispecific", "tetraspecific", etc. refer to the number of different antigen recognition site specificities (as opposed to the number of antigen recognition sites) present in a multivalent antibody construct of the invention. For example, a "monospecific" antibody construct's antigen recognition sites all bind the same epitope. A "bispecific" antibody construct has at least one antigen recognition site that binds a first epitope and at least one antigen recognition site that binds a second epitope that is different from the first epitope. A "multivalent monospecific" antibody construct has multiple antigen recognition sites that all bind the same epitope. A "multivalent bispecific" antibody construct has multiple antigen recognition sites, some number of which bind a first epitope and some number of which bind a second epitope that is different from the first epitope. In one embodiment of the invention, the antibody is a multivalent, bispecific antibody as shown in FIG. 9.

A "patient" or "subject" or "host" refers to either a human or non-human animal.

The term "pharmaceutical delivery device" refers to any device that may be used to administer a therapeutic agent or agents to a subject. Non-limiting examples of pharmaceutical delivery devices include hypodermic syringes, multichamber syringes, stents, catheters, transcutaneous patches, microneedles, microabraders, and implantable controlled release devices. In one embodiment, the term "pharmaceutical delivery device" refers to a dual-chambered syringe capable of mixing two compounds prior to injection.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

"Pharmaceutically-acceptable salts" refers to the relatively non-toxic, inorganic and organic acid addition salts of compounds.

The term "raft" or "lipid raft" refers to a lipid raft or a portion thereof which is a specialized cell membrane domain (see Simons et al., (2000) *Nature Reviews/Molecular Cell Biology* 1:31). In particular, the term "lipid raft" describes a cholesterol and glycosphingolipid-enriched microdomain of any membrane of a eukaryotic cell. Lipid rafts tend to be enriched in signaling molecules, with growth factor receptors and sensor molecules having been shown to migrate to lipid rafts after ligand binding or cross-linking. Lipid rafts are characterized by their resistance to solubilization at low temperature in nonionic detergents and can change in size and composition in response to intra- or extracellular stimuli. Specific protein-protein interactions may be favored within lipid rafts, resulting in modulation of signaling cascade activities in the case of, for example, plasma membrane cytokine receptors.

The potential effects of either "rafting" (defined herein as the incorporation of a membrane component, e.g., a receptor, into a lipid raft) or "de-rafting" (defined herein as removal, exit or barring of a membrane component, e.g., a receptor, from a lipid raft) a given receptor include modulation of cytokine receptor-mediated signaling (in some cases triggering apoptotic cell death), cellular localization of the receptor, and receptor abundance. Sometimes, lipid rafts may cluster; and it has been reported that such clustering is used both artificially and physiologically to trigger signaling cascades. In one embodiment, the receptor coupling agent of the invention brings two TNF family member receptors into a lipid raft. In another embodiment, the receptor coupling agent of the invention brings a TNF family receptor out of a lipid raft.

The term "receptor coupling agent" includes any agent or construct which can activate at least two distinct cell surface receptors. In one embodiment, the receptor coupling agent is a proteinaceous agent. Receptor coupling agents are used to enhance signaling capability of cell surface receptors. Receptor coupling agents of the invention are directed to TNF family receptors. In some instances, activation of at least two TNF family receptors by a receptor coupling agent can induce cell death. In one embodiment of the invention, the receptor coupling agent comprises a bispecific multivalent construct. In still another embodiment, the receptor coupling agent is a bispecific multivalent construct comprising an anti-LTβR binding moiety or specificity and an anti-TRAIL-R2 binding moiety or specificity. In another embodiment, the receptor coupling agent comprises binding specificity conferred by an anti-LTβR antibody (e.g. CBE11) and binding specificity conferred by an anti-TRAIL-R2 antibody (e.g. 14A2).

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

The term "synergistic" refers to a combination which is more effective than the additive effects of any two or more single agents. In one embodiment of the invention, the term synergistic includes a combination type of supra-additive inhibition in which both the LT-β-R agonist and chemotherapeutic agent individually have the ability to inhibit tumor volume. The term "potentiation" refers to a case in which simultaneous effect of two or more agents is greater than the sum of the independent effects of the agents.

"Treating" cancer in a subject or "treating" a subject having cancer refers to subjecting the subject to a pharmaceutical treatment, e.g., the administration of a drug, such that the extent of cancer is decreased or prevented. Treatment includes (but is not limited to) administration of a composition, such as a pharmaceutical composition, and may be performed either prophylactically, or subsequent to the initiation of a pathologic event.

The term "tumor volume" refers to the total size of the tumor, which includes the tumor itself plus affected lymph nodes if applicable. Tumor volume may be determined by a variety of methods known in the art, such as, e.g. by measuring the dimensions of the tumor using calipers, computed tomography (CT) or magnetic resonance imaging (MRI) scans, and calculating the volume using equations based on, for example, the z-axis diameter, or on standard shapes such as the sphere, ellipsoid, or cube.

II. Receptor Coupling Agent Targets

A limiting factor in the treatment of tumors with TNF family receptor activating agents is that often only a subset of tumors appear to be sensitive to such therapies. Receptor coupling agents can specifically activate TNF family receptors, and enhance receptor signaling by, for example, bringing the TNF family receptors into close proximity (for review on TNF receptors and the TNF family see Locksley et al. (2001) *Cell* 104:487). The invention provides receptor coupling agents which can target more than one TNF family receptor and enhance signaling, thus providing an improved method of treating cancer. As such, receptor coupling agents can deliver stronger or more complex signaling, and are therefore, more effective on a wider range of tumors, as shown in Example 3. In one embodiment, the receptor coupling agent increases the signal strength by increasing the number of receptors being brought together (Holler N Fau-Tardivel, et al., (2003) *Mol. Cell Biol.* 23:1428) In another embodiment, the receptor coupling agent activates two different TNF family receptors, thereby increasing the signal strength and triggering two different signal transduction cascades.

The receptor coupling agent of the invention comprises binding specificities which are directed to at least two distinct TNF family receptor members. Binding specificities are chosen according to the TNF family receptor members of interest which are to be targeted. For example, in one embodiment a receptor coupling agent comprises a first binding specificity for the TNF receptor TRAIL-R2 and a second binding specificity for the TNF receptor lymphotoxin-β receptor (LTβR). Examples of different types of TNF family receptors which may be targeted by a receptor coupling agent are described in more detail below.

A. TNF Receptors Containing a Death Domain

Receptor coupling agents may target TNF family receptors containing death domains, which may be useful for the treatment of cancer. A "death domain" or "DD" refers to a protein domain of certain TNF receptors comprising six conserved alpha helices. Death domain containing TNF receptors are primary targets of receptor coupling agents of the invention, and an example of such a construct is provided in the Examples section.

One example of a death domain receptor is Fas. Fas pathway molecules include any molecule involved in or related to a pathway leading to apoptosis or programmed cell death (PCD) induced by Fas. Fas pathway molecules include, but are not limited to Fas, the Fas ligand (FasL), and members of the TNFR superfamily of receptors. FADD, caspase 8, bid, and caspase 3 are also included as Fas pathway molecules. Fas pathway molecules may also be included in other groups as defined herein.

Some of the cytotoxic effects of lymphocytes are mediated by interaction of a lymphocyte-produced ligand with Fas-R (also known as DR-2, APO-1 and CD95; GenBank GI Nos. 4507583, 23510421, 23510423, 23510425, 23510427, 23510429, 23510431, and 23510434), a widely occurring cell surface receptor which has the ability to trigger cell death (see Nagata and Golstein, (1995) *Science* 267:1449-56). Binding of FasL to the Fas receptor leads to aggregation of the receptor on the cell membrane and specific recruitment of intracellular signaling molecules known as DISC, or death-inducing signal complex. The adaptor protein, FADD, binds to the intracellular death domain of Fas which leads to the recruitment of caspase-8, also known as PUCE or MACH. Fas-induced cell death may activate a pathway that alters mitochondrial permeability transition.

Cell killing by mononuclear phagocytes involves a ligand-receptor couple, TNF and its receptor, TNFR1 (also known as DR-1, CD120, p55-R; GenBank GI No. 4507575; see also U.S. Pat. No. 5,395,760), that is structurally related to Fas-R and its ligand (see also Vandenabeele et al., (1995) *Trends in Cell Biology* 5:392). Like other receptor-induced effects, cell death induction by the TNF receptors and Fas-R occurs via a series of protein-protein interactions, leading from ligand-receptor binding to the eventual inactivation of enzymatic effector functions, which in the case of these particular receptors results in cell death.

Under normal circumstances, Fas receptor engagement is accompanied by an infiltration of inflammatory cells and secondary necrosis and also provokes inflammation, e.g., hepatic inflammation, by inducing expression of cellular chemokines, e.g., hepatic chemokines, that recruit and activate immune cells leading to cell, e.g., hepatocyte, death in a proinflammatory milieu. In contrast, the receptor coupling agents of the current invention are designed to induce cell death in specific target cells. The targeted therapy of the invention may be more potent due to enhanced signalling and, therefore, may allow for treatment with lower doses of a drug. Such a strategy may minimize the negative consequences observed when apoptosis is systemically induced via activation of a single cell-surface cytokine receptor.

In addition to Fas-R and TNF-R1, other members of the TNF receptor family containing death domains include DR3 (also referred to as TRAMP, TR3, and Apo3, see GenBank GI Nos. 4507569, 23200021, 23200023, 23200025, 23200027, 23200029, 23200031, 23200033, 23200035, 23200037, and 23200039); TRAIL-R1 (also referred to as DR4 and Apo2, see GenBank GI No. 21361086); TRAIL-R2 (also referred to as DR5, see GenBank GI Nos. 22547116 and 22547119); p75NGF-R (also known as TNFRSF16; NCBI Reference Seq. NP_002498; GenBank GI No. 4505393); and DR6 (TRAIL-R3, GenBAnk GI No. 22547121), each containing death domains that directly initiate apoptosis.

There are four human TRAIL receptors termed TRAIL-R1-4. TRAIL-R1 and R2 also known as death receptors 4 and 5 (DR4-5) contain death domains in the intracellular region and are capable of triggering apoptosis (Wang and El-Deiry (2003) *Oncogene* 22:8628). TRAIL-R2 is preferred for human tumor therapy since its activation does not trigger hepatocyte apoptosis and hence should have reduced toxicity (Ichikaw et al. (2001) *Nat Med* 7:954). Thus receptor coupling agents which activate various TNF family receptors containing death domains, alone or in combination with any other TNFR, e.g., a non-death domain TNFR such as LTβR, are encompassed by the invention In one embodiment, a receptor coupling agent is used to decrease the toxic effects of death domain containing TNF receptors. While the activation of some death domain containing receptors, e.g. TNFR1 or Fas, has been shown to be toxic in vivo, it is likely that tethering these receptors to other TNF receptors may diminish toxicity and thus render a toxic antibody less toxic. For example, if raft association is critical for the full signaling of TNFR1, de-rafting by tethering to a non-rafted receptor may be sufficient to reduce anti-TNFR1 toxicity. In one embodiment, a receptor coupling agent comprises a binding moiety comprising an anti-LTβR antibody, or antigen binding fragment thereof, and a binding moiety directed to an anti-TNF family receptor containing a death domain.

B. Non-Death Domain Receptors

Receptor coupling agents of the invention may target TNF family receptors which do not contain the death domain. The activation of non-death domain containing TNF receptors for the treatment of solid tumors, specifically an anti-LTβR agonist monoclonal antibody (mAb), also shows potential as an anti-tumor therapy (Browning, et al. (1996) *J Exp Med* 183: 867, Wilson and Browning (2003) *Cell Death Duff* 9:1321).

One example of a non-death domain containing TNF receptor family member is LTβR. LTβR is involved in the control of the maturation status of various specialized stromal cells in the immune system and plays a critical role during the development of the stromal elements of the lymph node anlagen (Mebius (2003) *Nat Rev Immunol* 3:292). It has been proposed that activation of a developmental program in epithelial or fibroblastoid cells in the context of a transformed cell is detrimental for their survival and this action may account for some of the anti-tumor activity of LTβ receptor activation. These receptors can also initiate inflammatory programs that involve chemokine release or promote immunological anti-tumor responses (Yu et al. (2004) *Nat Immunol* 5:141, Baud (2001) *Trends Cell Biol* 11:372). Such release may affect the inflammatory status of the tumor and/or invoke infiltration of lymphoid elements promoting an immunological reaction to the tumor. Thus receptor coupling agents which activate of various TNF family receptors lacking death domains, alone or in combination with TNF receptors containing death domains, are encompassed by the invention.

In addition to LTβR, other examples of TNF receptors which lack a death domain include Fn14 (also referred to as TWEAK-R; see Applicant's co-pending application WO 02/22166); RANK (see NCBI Accession Nos. AAB86809, AF018253); TAJ (also referred to as TROY, see NCBI Accession Nos. AAF71828, AAH47321, AAK28395); EDAR (see NCBI Accession Nos. AAD50076, AAD50077, AF130988); XEDAR (see NCBI Accession Nos. AAG28761, AAH34919, AAN73210); and CD40 (also referred to as CD40L receptor, see NCBI Accession Nos. AAH12419, AAH64518, AAR84238).

A subgroup among TNF receptors lacking a death domain includes TNF receptors which are involved in tissue differentiation, including development and wound healing. Several TNF receptors have well-defined developmental roles, e.g. LTβR, RANK, EDAR and XEDAR (Mebius (2003) *Nat Rev Immunol* 3:292; Theill et al., (2002) *Ann Rev Immunol* 20:795; Larikkala et al., (2002) *Development* 129:2541; Rennert (2000) *J Exp Med* 192:1677). Differentiation is the process by which normal cells undergo physical and structural changes as they develop to form different tissues of the body. Differentiation programs may affect tumors in several ways. First, TNF receptors involved in tissue differentiation have the potential to directly slow tumor growth by altered cell cycle progression. Second, the program in the context of transformation may lead to cell cycle conflict and default apoptosis. Third, such conflicting input may render a cell more sensitive to chemotherapy.

Examples of TNF receptor molecules shown to mediate tissue differentiation which may be targeted by a receptor coupling agent to enhance TNF signalling include the following: RANK (also known as TNFRSF11A; GenBank GI No. 4507565; Accession No. AF018523; U.S. Pat. Nos. 6,562, 948; 6,537,763; 6,528,482; 6,479,635; 6,271,349; 6,017,729); EDAR1 (also known as Downless; GenBank GI No. 11641231; Accession No. AF130988; U.S. Pat. No. 6,355,782); and TAJ/Troy/Trade (also known as TNFRSF19; GenBank GI Nos. 23238202 and 23238204; Accession No. AF167555). In addition, XEDAR (also known as EDA-A2R; GenBank GI No. 11140823; Accession No. AF130988) signaling is involved in the process of ectodermal differentiation. XEDAR plays a major role in the activation of the NF-kappaB and JNK pathways. Fn14 has been shown to be involved in nerve regeneration (Tanabe et al. (2003) *J. Neurosci.* 23:9675). Fn14 is also known as TWEAKR and TNFRSF12A (see GenBank GI No. 7706186; U.S. Pat. No. 6,727,225; US Patent Application Publication No. 2004/0033225A1). Thus receptor coupling agents which activate various TNF family receptors involved in tissue differentiation are encompassed by the invention.

C. Immune Regulation Receptors

The TNF receptor superfamily also contains several receptors involved in immune regulation, which can be targeted by the constructs of the present invention. Such receptors include TNFR2 (also known as TNFRSF1B; GenBank GI No. 4507577), HVEM (also known as TNFRSF14; GenBank GI No. 23200041), CD27 (also known as TNFRSF7; GenBank GI No. 4507587), CD30 (also known as TNFRSF8; GenBank GI Nos. 4507589 and 23510437), CD40 (also known as TNFRSF5; GI Nos. 4507581 and 23312371), 4-1BB (also known as TNFRSF9; GI No. 5730095), OX40 (also known as TNFRSF4; GI No. 4507579), GITR (also known as TNFRSF18; GenBank GI Nos. 4759246, 23238194 and 23238197), TACI (also known as TNFRSF13B; GI No. 6912694), BAFF-R (also known as TNFRSF13C; GI No. 16445027), BCMA (also known as TNFRSF17; GI No. 23238192), and RELT (also known as TNFRSF19L; GI Nos. 21361873 and 23238200). Additional TNF family receptors involved in immune regulation include TRAIL-R3 and TRAIL-R4. Thus receptor coupling agents which activate of various TNF family receptors involved in immune regulation are encompassed by the invention.

D. Other TNF Receptors

Other target TNF family receptors may be selected for their role in tumor formation, and can be identified using existing RNA databases of receptor expression in various cell types which allow one to define TNF family receptors that are present or ideally overexpressed on various tumors. Moreover, existing RNA databases provide an additional advantage in that the pair of TNF family receptors could be optimized by identifying those receptor pairs that are more uniquely expressed on a tumor type or subset of tumors but are not abundant on normal tissues, especially liver and vasculature. In such a manner receptor pairs (or more) are identified that could deliver a potent signal to the tumor and spare normal tissues. Methods of testing the efficacy of selected receptors are described in more detail below and in the Examples section.

Receptor coupling agents of the invention target at least two distinct TNF receptors. Target TNF receptors are selected based on the individual characteristics of the receptor. For example, a receptor coupling agent may target two TNF receptors which are involved in differentiating events, and, therefore, may be effective at treating solid tumors. Other examples of combinations of TNF receptors which the receptor coupling agent of the invention may be directed to are described below.

Non-Death Domain/Death Domain TNF Receptor Coupling Agent

In one embodiment of the invention, the receptor coupling agent targets and activates one TNF receptor which contains a death domain and one TNF receptor which does not contain a death domain. Examples of combinations of targeted non-death domain/death-domain containing TNF receptors include: LTBR/TRAIL-R1; LTBR/TRAIL-R2; LTBR/p75NGF-R; Fn14/p75NGF-R; and p75NGF-R/TAJ. Coupling a death domain containing TNF receptor to a non-death domain containing receptor may further decrease the toxicity of the activation of the death domain containing receptor.

In another embodiment, at least one of the non-death domain containing TNF receptors is involved in cell differentiation, including, but not limited to LTBR, RANK, and Fn14. As described in detail below, LTBR, RANK, and Fn14 are each involved in cell differentiation. Examples of non-death domain/death-domain containing TNF receptors, wherein the non-death domain TNF receptor is involved in cell differentiation include, for example, LTBR/p75NGF-R; Fn14/p75NGF-R; and TAJ/p75NGF-R.

Non Death Domain/Non Death Domain TNF Receptor Coupling Agent

In one embodiment of the invention, the receptor coupling agent targets and activates two distinct TNF receptors, neither of which contains a death domain. Examples of combinations of non-death domain/non-death domain containing TNF receptors targeted by a receptor coupling agent include: LTBR/Fn14; LTBR/RANK; Fn14/TAJ; LTBR/EDAR; LTBR/XEDAR; RANK/EDAR; RANK/XEDAR; TAJ/EDAR; TAJ/XEDAR; and LTBR/CD40.

In another embodiment, at least one of the non-death domain/non-death domain containing TNF receptors is involved in cell differentiation. For example, the receptor coupling agent may be directed to LTBR and Fn14. Fn14 is the receptor to TWEAK, a TNF ligand with the capacity to induce cell death in the adenocarcinoma cell line HT29 (see Chicheportiche et al. (1997) *J. Biol. Chem.* 272:32401). The apoptotic activity of TWEAK is mediated by Fn14. Fn14 is also involved in tissue remodeling after injury. The molecular mechanisms found in tissue remodeling are similar to tissue differentiation, and such programs may not be favorable to tumor growth. In another example, a receptor coupling agent may be directed to LTBR and RANK. RANK signaling triggers differentiation of mammary epithelium and, therefore, may have enhanced activity when coupled to another differentiation inducing agent. Thus, enhancing RANK and LTBR signalling using a receptor coupling agent may be useful in preventing tumor growth.

In addition to LTBR, RANK, and Fn14, TAJ/TROY plays a role in tissue differentiation, specifically in the regulation of axonal regeneration (Shao et al. (2005) *Neuron* 45:353). TAJ is involved in the repression of neurite outgrowth in response to myelin components, i.e. effectively a differentiation event. As Fn14 is expressed in post neuronal injury (Tanabe et al. (2003) *J. Neurosci.* 23:9675), the combined signal with TAJ may be used to treat tumors associated with the central nervous system. Thus, in one embodiment, a receptor coupling agent may target TAJ and Fn14.

Other examples of combinations of non-death domain containing TNF receptors which are involved in tissue differentiation, and, therefore, may be beneficial in the inhibition of tumor growth, include, but are not limited to, LTBR/EDAR; LTBR/XEDAR; RANK/EDAR; RANK/XEDAR; TAJ/EDAR; and TAJ/XEDAR.

Death Domain/Death Domain TNF Receptor Coupling Agent

In one embodiment of the invention, the receptor coupling agent binds two distinct TNF receptors, which both contain a death domain. TRAIL-R1/TRAIL-R2 is an example of a combination of death domain/death domain containing TNF receptors which may be targeted by a receptor coupling agent.

Immunological TNF Receptor Coupling Agent

In one embodiment of the invention, the receptor coupling agent binds two distinct TNF receptors which are involved in an immune response. Examples of combinations of immune response TNF receptors which mediate B cell responses, include CD40/CD27; CD40/BAFF-R; CD40/BCMA; and BAFF-R/CD27. Examples of combinations of TNF receptors which mediate T cell immune responses include CD27/CD30; CD27/OX-40; CD27/41BB; and OX-40/41BB.

III. Receptor Coupling Agents

A receptor coupling agent is capable of inducing formation of a heteromeric receptor complex comprising a receptor coupling agent and at least two distinct TNF family receptors. The TNF family receptors have common signaling modalities as well as specialized transduction mechanisms unique to specific receptors. These signal transduction pathways are highly complex with three or more pathways being activated in many cases. Use of a receptor coupling agent to induce formation of a heteromeric receptor complex may more effectively limit tumor growth. For example, a receptor coupling agent targeting the relatively unique ability of LTβR to activate the alternate NFκB pathway (Dejardin et al., (2002) *Immunity* 17:525) coupled with caspase activation stemming from a death domain containing receptor may (e.g., TRAIL-R2) may result in reduced tumor growth. In addition, such agents may juxtapose two different TNF family receptors into one complex resulting in the co-assembly of signal transduction machinery elements into aggregates that are novel and even potentially non-physiological.

Receptor coupling agents of the invention may be used to re-orient a TNF family receptor into a unique cell membrane environment which affects signaling. The signaling capability of some receptors depends on their location within specialized membrane environments, such as within lipid rafts. Examples of such TNF family receptors include Fas and possibly the TNFRI receptor (Muppidi and Siegel (2004) *Nat Immunol* 5:182, Legler et al., (2003) *Immunity* 18:655). TRAIL receptors also exhibit complex localization patterns (Zhang et al. (2000) *J Immunol* 164:3961). A receptor coupling agent which couples one receptor that normally resides within a lipid raft to another receptor that is not normally rafted may force the second receptor into the raft environment and enhance its signaling capability Likewise, a receptor coupling agent which couples one receptor which normally resides outside a lipid raft to another receptor which is normally inside the raft may force the first receptor outside of the raft environment and decrease the signaling capacity.

The receptor coupling agent of the invention may enhance signal strength, forming new non-physiological heteromeric receptor complexes that embody novel signaling characteristics and/or relocalize a receptor into an environment where signaling is more, or less, effective. In one embodiment, the receptor coupling agent of the invention is used to bring a TNF family receptor into a lipid raft in which the TNF family receptor is not normally found. In another embodiment, the receptor coupling agent is able to re-locate a TNF family receptor outside of a lipid raft.

Receptor coupling agents of the invention include any agent which is capable of forming a heteromeric complex with at least two distinct TNF receptors. The receptor coupling agent comprises at least two binding specificities which are directed to two distinct TNF receptors. A binding specificity includes any entity which affects receptor signaling, e.g., enhances or decreases receptor signaling. Examples of binding specificity agents which can be used to prepare a receptor coupling agent of the invention include, but are not limited to, antibodies, antigen-binding fragments thereof, ligands to the TNF receptor, or any combination thereof.

A. Antibodies

In one embodiment, the receptor coupling agent of the invention contains binding specificities or moieties comprising or derived from at least two antibodies, or antigen binding fragments thereof, directed to TNF receptor family members. A receptor coupling agent which is a bifunctional construct may contain sequences obtained from a parental antibody directed to the TNF receptors of interest. Bifunctional constructs that can engage and activate two TNF receptors offer a novel approach, as such constructs embody the capability to activate two different TNF receptors and thus avoid the complications of packaging two antibodies into one drug cocktail, a complex process from a drug manufacturing standpoint.

In one embodiment, the receptor coupling agent is a multivalent construct comprising agonists of TNF family receptors, wherein the receptor coupling agent comprises at least two domains that are capable of binding to each receptor and inducing an activating signal. The antibody constructs of the invention can include a heavy chain containing two or more variable regions comprising antigen recognition sites specific for binding a TNF family receptor and a light chain containing one or more variable regions comprising antigen recognition sites specific for a TNF family receptor. Antibody constructs may also be constructed to comprise only heavy chains or light chains containing two or more variable regions comprising CDRs specific for binding a distinct TNF family receptor. In one embodiment, the multivalent antibody comprises antigen binding sites or binding moieties which can bind to TRAIL-R2 and LTβR.

In one aspect, the present invention provides for multivalent antibody constructs that are TNF receptor agonists, including, but not limited to, LTβR and TRAIL-R2 agonists. In one embodiment, a multivalent antibody construct comprises at least one antigen recognition site specific for a LTβR epitope. In another embodiment, a multivalent antibody construct comprises at least one antigen recognition site specific for a TRAIL-R2 epitope. In certain embodiments, at least one of the antigen recognition sites is located within a scFv domain, while in other embodiments, all antigen recognition sites are located within scFv domains.

In certain embodiments, the receptor coupling agent is bispecific. In other embodiments, the construct is specific for at least two members of the TNF family of receptors, including, but not limited, to, LTβR epitopes and TRAIL-R2 epitopes. In any of the multispecific constructs, at least one antigen recognition site may be located on a scFv domain, and in certain embodiments, all antigen recognition sites are located on scFv domains. In still other embodiments, the antibody constructs of the invention comprise the polynucleotide sequences described in SEQ ID NOs: 5 and 7 (LT-BS1 construct).

Binding specificities or moieties comprising antigen recognition sites or entire variable regions may be derived from one or more parental antibodies. The parental antibodies can include naturally occurring antibodies or antibody fragments, antibodies or antibody fragments adapted from naturally occurring antibodies, antibodies constructed de novo using sequences of antibodies or antibody fragments known to be specific for the LT-beta receptor. Sequences that may be derived from parental antibodies include heavy and/or light chain variable regions and/or CDRs, framework regions or other portions thereof. In one embodiment of the invention, the parental antibodies used to construct a receptor coupling agent are an anti-TRAIL-R2 antibody, for example 14A2, and an anti-LTβR antibody, for example CBE11.

Multivalent, multispecific antibodies may contain a heavy chain comprising two or more variable regions and/or a light chain comprising one or more variable regions wherein at least two of the variable regions recognize different epitopes on the LT-beta receptor.

Receptor coupling agents comprising multivalent, anti-TNF receptor antibodies may be constructed in a variety of different ways using a variety of different sequences derived from parental anti-LTβR antibodies, including murine or humanized BHA10 (WO 04/002431; see also Browning et al., (1995) *J. Immunol.* 154: 33; Browning et al., (1996) *J. Exp. Med.* 183:867), murine or humanized CBE11 (U.S. Pat. No. 6,312,691 and WO 02/30986, respectively), and/or parental anti-TRAIL-R2 murine or chimeric 14A2 (see SEQ ID NO: 1 and 3).

Examples of murine anti-LTβR antibodies which can be used for the receptor coupling agent of the invention include: BKA11, CDH10, BCG6, AGH1, BDA8, CBE11 and BHA10. The following hybridoma cell lines producing monoclonal anti-LT-β-R antibodies may be used to produce anti-LTβR antibodies from which to derive antibody construct sequences, which have been previously deposited with the American Type Culture Collection (ATCC) according to the provisions of the Budapest Treaty and have been assigned the indicated ATCC accession numbers:

| Cell Line | mAb Name | Accession No. |
|---|---|---|
| a) AG.H1.5.1 | AGH1 | HB 11796 |
| b) BD.A8.AB9 | BDA8 | HB 11798 |
| c) BC.G6.AF5 | BCG6 | B 11794 |
| d) BH.A10 | BHA10 | B 11795 |
| e) BK.A11.AC10 | BKA11 | B 11799 |
| f) CB.E11.1 | CBE11 | B 11793 |
| g) CD.H10.1 | CDH10 | B 11797 |

Examples of humanized anti-LTβR antibodies which can be used in conjunction with the present invention include humanized CBE11 and humanized BHA10. The following hybridoma cell lines may be used to produce anti-LTβR antibodies from which to derive antibody construct sequences, which have been previously deposited with the American Type Culture Collection (ATCC) according to the provisions of the Budapest Treaty and have been assigned the indicated ATCC accession numbers: PTA-3357 and 3765 (humanized CBE11, see WO 02/30986) and PTA-4726 (humanized BHA10, see WO 04/002431).

Other examples of anti-TNF receptor antibodies which are compatible with the receptor coupling agents of the invention may be derived from antibodies directed to TNF receptors containing a death domain. A number of antibodies have been generated to death domain containing TNF receptors and are well known in the art. Such antibodies include anti-TNF-R1 monoclonal antibodies (R&D systems anti-TNF-R1; Tularik mAb #985, U.S. Pat. Nos. 6,110,690; 6,437,113), anti-Fas receptor mAb CH-11 (U.S. Pat. No. 6,312,691; WO 95/10540), anti-DR3 antibodies (U.S. Pat. No. 5,985,547; Johnson, et al., (1984) ImmunoBiology of HLA, ed. Dupont, B. O., Springer, New York; U.S. Pat. Nos. 6,462,176; 6,469,166), and anti-TRAIL-R antibodies (U.S. Pat. Nos. 5,763,223; 6,072,047; 6,284,236; 6,521,228; 6,569,642; 6,642,358; and U.S. Pat. No 6,417,328).

A number of antibodies have been also raised to TNF receptors involved in tissue differentiation and are known in the art. Examples of anti-TNF receptor antibodies specific to TNF receptors involved in tissue differentiation include: anti-RANK monoclonal antibodies (Immunex—U.S. Pat. Nos. 6,562,948; 6,537,763; 6,528,482; 6,479,635; 6,271,349; 6,017,729; Komed—WO 03/080671), anti-EDAR polyclonal (anti-human) and monoclonal (anti-mouse) antibodies (R&D Systems—MAB745, BAF157; Elomaa et al. (2001) *Human Molecular Genetics.* 10:953), anti-XEDAR monoclonal and polyclonal antibodies (R&D Systems—MAB1093 and AF1093), anti-Fn14 monoclonal antibodies (Nakayama et al. (2003) *J. Immunology* 170:341; ITEM-1, ITEM-2, and ITEM-4 clones available from eBioscience), anti-TROY antibody (T3323 from Sigma-Aldrich), and anti-NGFR (anti-rodent) antibodies (Chemicon USA).

A number of antibodies have been also raised to TNF receptors involved in immune regulation and are known in the art. Examples of anti-TNF receptor antibodies specific to TNF receptors involved in immune regulation include: anti-HVEM antibodies (HGSI—WO 03/086301), anti-CD40 antibodies (Biogen—WO 97/20063; Chiron—U.S. Pat. Nos. 5,677,165; 5,874,082; 6,004,552; 6,056,959; 6,315,998; US Application Publication No. 2002/0106371; US Application Publication Nos. 2003/0059427; US20030118588A1; 2003/0211100A1; US2002020142358A1; U.S. Pat. No. 6,312,693; U.S. Pat. No. 6,051,228; Fanslow et al.—U.S. Pat. No. 5,801,227), anti-4-1BB (PCT Publication No. WO 03/084999; EP 0948353; U.S. Pat. No. 6,210,669; Genecraft—WO 03/083069), and anti-BAFF-R antibodies (rabbit polyclonal—ProSci catalog #3097), among many other antibodies raised to immune regulation receptors.

Multivalent constructs directed to TNF receptors may be developed by one of skill in the art using routine recombinant DNA techniques, for example as described in PCT International Application No. PCT/US86/02269; European Patent Application No. 184,187; European Patent Application No. 171,496; European Patent Application No. 173,494; PCT International Publication No. WO 86/01533; U.S. Pat. No. 4,816,567; European Patent Application No. 125,023; Better et al., (1988) *Science* 240:1041-1043; Liu et al., (1987) *Proc. Natl. Acad. Sci. USA* 84:3439-3443; Liu et al., (1987) *J. Immunol.* 139:3521-3526; Sun et al. (1987) *Proc. Natl. Acad. Sci. USA* 84:214-218; Nishimura et al., (1987) *Cancer Res.* 47:999-1005; Wood et al. (1985) *Nature* 314:446-449; Shaw et al., (1988) *J. Natl. Cancer Inst.* 80:1553-1559); Morrison (1985) *Science* 229:1202-1207; Oi et al., (1986) *BioTechniques* 4:214; U.S. Pat. No. 5,225,539; Jones et al., (1986) *Nature* 321:552-525; Verhoeyan et al., (1988) *Science* 239: 1534; Beidler et al., (1988) *J. Immunol.* 141:4053-4060; and Winter and Milstein, (1991) *Nature* 349:293-99). Preferably non-human antibodies are "humanized" by linking the non-human antigen binding domain with a human constant domain (e.g. Cabilly et al. U.S. Pat. No. 4,816,567; Morrison et al. (1984) *Proc. Natl. Acad. Sci. U.S.A.,* 81:6851-55).

Other methods which may be used to prepare multivalent anti-TNF receptor antibody constructs are described in the following publications: Ghetie et al. (2001) *Blood* 97:1392-1398; Wolff et al. (1993) *Cancer Research* 53:2560-2565; Ghetie et al. (1997) *Proc. Natl. Acad. Sci.* 94:7509-7514; Kim et al. (2002) *Int. J. Cancer* 97(4):542-547; Todorovska et al. (2001) *Journal of Immunological Methods* 248:47-66; Coloma et al. (1997) *Nature Biotechnology* 15:159-163; Zuo et al. (2000) *Protein Engineering (Suppl.)* 13(5):361-367; Santos et al. (1999) *Clinical Cancer Research* 5:3118s-3123s; Presta (2002) *Current Pharmaceutical Biotechnology* 3:237-256; van Spriel et al. (2000) *Review Immunology Today* 21(8) 391-397.

B. TNF Ligands

The receptor coupling agent of the invention also includes binding specificities comprising at least two conventional TNF family ligands coupled together. Examples of TNF family ligands include, but are not limited to, TNF-alpha (NP_000585.2, GI No. 25952111) LT-alpha, (NP_000586.2, GI No. 6806893), FasL (NP_000630; GenBank GI No. 4557329), APO-3L (NP_003800, GI No. 4507597; NP_694557, GI No. 23510441), TRAIL (APO-2L, NP_003801, GI No. 4507593), RANKL (TNFSF11, NP_003692, GI No. 4507595; NP_143026, GI No. 14790152), EDAR1 & XEDAR ligand (ED1, NP_001390, GI No. 4503449; Monreal et al. (1998) *Am J Hum Genet.*

63:380), Fn14 ligand (APO-3L/TWEAK), Troy/Trade ligand NGF (NGF-β, NP_002497, GI No. 4505391), NGF family (NGF-2/NTF3, NP_002518, GI No. 4505469; NTF5, NP_006170, GI No. 5453808; BDNF: NP_001700, GI No. 25306267; NP_733927, GI No. 25306235; NP_733928, GI No. 25306253; NP_733929, GI No. 25306257; NP_733930, GI No. 25306261; NP_733931, GI No. 25306264; IFRD1, NP_001541, GI No. 4504607), TNFRII ligand (TNF, above), HVEM ligand (NP_003798, GI No. 25952144; NP_742011, GI No. 25952147), CD27L (CD70 antigen, NP_001243, GI No. 4507605), CD30L (CD153, NP_001235, GI No. 4507607), CD40L (CD154, NP_000065, GI No. 4557433), 4-1BB-L (ILA ligand, NP_003802, GI No. 4507609), OX40L (CD134L, NP_003317, GI No. 4507603), GITRL (AITRL/TL6, NP_005083, GI No. 4827034), and BAFF (TALL1, NP_006564, GI No. 5730097).

C. Antibody/Receptor Combinations

Receptor coupling agents of the invention also include any combination of the above-mentioned anti-TNF receptor antibodies and TNF ligands. For example, the receptor coupling agent may comprise a combination of a ligand-Fc construct coupled to an antibody to a TNF family receptor in a form that creates a molecule with two trimeric ligands and three antibodies or any higher order complexes. In one embodiment, the first binding specificity comprises at least two trimeric ligand-Fc constructs that are commonly formed from three dimeric Fc domains and six ligand molecules. In this case, second binding specificity would be comprised from the three antibody molecules. The invention also includes a combination of a conventional ligand (not an Ig fusion protein) to a TNF family receptor coupled to an antibody to a TNF family receptor.

IV. Methods of Making Receptor Coupling Agents

Efficacy of receptor coupling agents directed to a combination of TNF receptors can be assessed by standard assays, including in vitro assays which assess cytotoxicity or growth inhibition, soft agar colony formation assays and 3-D tumor culture systems, such as those established for breast tumor. Efficacy can also be validated by in vivo xenograft models. The use of human primary lung, liver and endothelial cell lines allows for in vitro prediction of gross toxicity. Typically, induced apoptosis and display of surface adhesion molecules such as VCAM or ICAM serve as potential markers. For example IL-8 and/or IP-10 serve as good markers for toxicity or induction of a pro-inflammatory program that could be detrimental.

Cancer cell lines which can be used to test the receptor coupling agent of the invention are known in the art. Examples of cell lines which are often used as a standard model of colorectal carcinoma, include, for example, the HT29 cell line for evaluation of TNF receptor activating agents. This cell line exists in two variants, HT29 and WiDr and the HT29 cell line has been employed by the National Cancer Institute in their screening panel for potential new chemotherapeutic agents. As such it is a good tool to evaluate the potential of some anticancer agents. Examples of other colorectal cell lines include KM20L2, LS174T, and CACO-2. Examples of breast cancer cell lines which can be used to test the efficacy of the receptor coupling agent include MCF7 and MDA231. Examples of cervical cancer cells line which can be used to test the efficacy of the receptor coupling agent include Hela and ME180. In addition, an example of a melanoma cell line includes A375, and example of a rhabdomyosarcoma includes RD, and an example of a sarcoma cell line is SAOS-2.

Candidate antibody constructs may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6. The following Examples provide assays for determining the efficacy of receptor coupling agent activation by candidate anti-TRAIL-R2 and LTβR agonist antibody constructs.

The receptor coupling agents described above may be purified to a suitable purity for use as a pharmaceutical composition. Generally, a purified composition will have one species that comprises more than about 85 percent of all species present in the composition, more than about 85%, 90%, 95%, 99% or more of all species present. The object species may be purified to essential homogeneity (contaminant species cannot be detected in the composition by conventional detection methods) wherein the composition consists essentially of a single species. A skilled artisan may purify a polypeptide of the invention using standard techniques for protein purification, for example, immunoaffinity chromatography, size exclusion chromatography, etc. in light of the teachings herein. Purity of a polypeptide may be determined by a number of methods known to those of skill in the art, including for example, amino-terminal amino acid sequence analysis, gel electrophoresis and mass-spectrometry analysis.

In one embodiment, the receptor coupling agents of the invention can be conjugated to a chemotherapeutic agent to inhibit tumor volume in a supra-additive manner. Exemplary chemotherapeutics that can be conjugated to the antibodies of the present invention include, but are not limited to radioconjugates (90Y, 131I, 99mTc, 111In, 186Rh, et al.), tumor-activated prodrugs (maytansinoids, CC-1065 analogs, clicheamicin derivatives, anthracyclines, vinca alkaloids, et al.), ricin, diptheria toxin, pseudomonas exotoxin.

In some embodiments, the receptor coupling multivalent antibodies and antibody fragments of the invention may be chemically modified to provide a desired effect. For example, pegylation of antibodies and antibody fragments of the invention may be carried out by any of the pegylation reactions known in the art, as described, for example, in the following references: *Focus on Growth Factors* 3:4-10 (1992); EP 0 154 316; and EP 0 401 384 (each of which is incorporated by reference herein in its entirety). Preferably, the pegylation is carried out via an acylation reaction or an alkylation reaction with a reactive polyethylene glycol molecule (or an analogous reactive water-soluble polymer). A preferred water-soluble polymer for pegylation of the antibodies and antibody fragments of the invention is polyethylene glycol (PEG). As used herein, "polyethylene glycol" is meant to encompass any of the forms of PEG that have been used to derivatize other proteins, such as mono (Cl—ClO) alkoxy- or aryloxy-polyethylene glycol.

Methods for preparing pegylated antibodies and antibody fragments of the invention will generally comprise the steps of (a) reacting the antibody or antibody fragment with polyethylene glycol, such as a reactive ester or aldehyde derivative of PEG, under conditions whereby the antibody or antibody fragment becomes attached to one or more PEG groups, and (b) obtaining the reaction products. It will be apparent to one of ordinary skill in the art to select the optimal reaction conditions or the acylation reactions based on known parameters and the desired result.

Pegylated antibodies and antibody fragments may generally be used to treat conditions that may be alleviated or modulated by administration of the antibodies and antibody fragments described herein. Generally the pegylated antibodies and antibody fragments have increased half-life, as compared to the nonpegylated antibodies and antibody fragments. The pegylated antibodies and antibody fragments may be employed alone, together, or in combination with other pharmaceutical compositions.

In other embodiments of the invention the antibodies or antigen-binding fragments thereof are conjugated to albumen using art recognized techniques. In another embodiment of the invention, multivalent antibodies, or fragments thereof, are modified to reduce or eliminate potential glycosylation sites. Such modified antibodies are often referred to as "aglycosylated" antibodies. In order to improve the binding affinity of an antibody or antigen-binding fragment thereof, glycosylation sites of the antibody can be altered, for example, by mutagenesis (e.g., site-directed mutagenesis). "Glycosylation sites" refer to amino acid residues which are recognized by a eukaryotic cell as locations for the attachment of sugar residues. The amino acids where carbohydrate, such as oligosaccharide, is attached are typically asparagine (N-linkage), serine (O-linkage), and threonine (O-linkage) residues. In order to identify potential glycosylation sites within an antibody or antigen-binding fragment, the sequence of the antibody is examined, for example, by using publicly available databases such as the website provided by the Center for Biological Sequence Analysis (for predicting N-linked glycoslyation sites and for predicting O-linked glycoslyation sites). Additional methods for altering glycosylation sites of antibodies are described in U.S. Pat. Nos. 6,350,861 and 5,714,350.

In yet another embodiment of the invention, receptor coupling agents which are multivalent antibodies or fragments thereof can be altered wherein the constant region of the antibody is modified to reduce at least one constant region-mediated biological effector function relative to an unmodified antibody. To modify an antibody of the invention such that it exhibits reduced binding to the Fc receptor (FcR), the immunoglobulin constant region segment of the antibody can be mutated at particular regions necessary for FcR interactions (see e.g., Canfield et al. (1991) *J. Exp. Med.* 173:1483; and Lund et al., (1991) *J. of Immunol.* 147:2657). Reduction in FcR binding ability of the antibody may also reduce other effector functions which rely on FcR interactions, such as opsonization and phagocytosis and antigen-dependent cellular cytotoxicity.

In a particular embodiment the invention further features receptor coupling multivalent antibodies having altered effector function, such as the ability to bind effector molecules, for example, complement or a receptor on an effector cell. In particular, the humanized antibodies of the invention have an altered constant region, e.g., Fc region, wherein at least one amino acid residue in the Fc region has been replaced with a different residue or side chain thereby reducing the ability of the antibody to bind the FcR. Reduction in FcR binding ability of the antibody may also reduce other effector functions which rely on FcR interactions, such as opsonization and phagocytosis and antigen-dependent cellular cytotoxicity. In one embodiment, the modified humanized antibody is of the IgG class, comprises at least one amino acid residue replacement in the Fc region such that the humanized antibody has an altered effector function, e.g., as compared with an unmodified humanized antibody. In particular embodiments, the humanized antibody of the invention has an altered effector function such that it is less immunogenic (e.g., does not provoke undesired effector cell activity, lysis, or complement binding), and/or has a more desirable half-life while retaining specificity for LTβR.

Alternatively, the invention features receptor coupling multivalent humanized antibodies having altered constant regions to enhance FcR binding, e.g., FcγR3 binding. Such antibodies are useful for modulating effector cell function, e.g., for increasing ADCC activity, e.g., particularly for use in oncology applications of the invention. As used herein, "antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. of the antibody, e.g., a conjugate of the antibody and another agent or antibody.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (Glover ed., 1985); *Oligonucleotide Synthesis* (Gait ed., 1984); Mullis et al. U.S. Pat. No. 4,683,195; *Nucleic Acid Hybridization* (Hames & Higgins eds. 1984); *Transcription And Translation* (Hames & Higgins eds. 1984); *Culture Of Animal Cells* (Freshney, Alan R. Liss, Inc., 1987); *Immobilized Cells And Enzymes* (IRL Press, 1986); Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology, Vols.* 154 and 155 (Wu et al. eds.), *Immunochemical Methods In Cell And Molecular Biology* (Mayer and Walker, eds., Academic Press, London, 1987); *Handbook Of Experimental Immunology,* Volumes I-IV (Weir and Blackwell, eds., 1986); *Manipulating the Mouse Embryo,* (Cold Spring Harbor Laboratory Press, Cold Spring Harbor, N.Y., 1986).

Production of muBHA10 and muCBE11 variable regions, murine-human BHA10 and CBE11 chimeric antibodies, reshaped BHA10 and CBE11 variable domains, expression vectors encoding huBHA10 and huCBE11, pentameric chCBE11 antibodies, and methods of purifying and assaying the same have been previously described in Applicants' copending applications PCT publication no. WO 96/22788, PCT publication WO 02/30986, PCT application no. WO 04/002431, and WO 04/058191, which are each hereby incorporated by reference in their entirety.

V. Pharmaceutical Compositions

The invention provides pharmaceutical compositions comprising the above-described receptor coupling agents. In certain embodiments, the pharmaceutical compositions may further comprise a chemotherapeutic agent. In one aspect, the present invention provides pharmaceutically acceptable compositions which comprise a therapeutically-effective amount of one or more of the compounds described above, formulated together with one or more pharmaceutically acceptable carriers (additives) and/or diluents. In another aspect, certain embodiments, the compounds of the invention may be administered as such or in admixtures with pharmaceutically acceptable carriers and may also be administered in conjunction with other chemotherapeutic agents. Conjunctive (combination) therapy thus includes sequential, simultaneous and separate, or co-administration of the active compound in a way that the therapeutic effects of the first administered one is not entirely disappeared when the subsequent is administered.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art. While it is possible for a compound of the present invention to be administered alone, it is preferable to administer the compound as a pharmaceutical formulation (composition). The compounds according to the invention may be formulated for administration in any convenient way for use in human or veterinary medicine, by analogy with other pharmaceuticals.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. In one embodiment, the pharmaceutical compositions are formulated for parenteral administration. In one embodiment, the pharmaceutical composition is formulated for intraarterial injection. In another embodiment, the pharmaceutical compositions are formulated for systemic administration.

In other cases, the compounds of the present invention may contain one or more acidic functional groups and, thus, are capable of forming pharmaceutically-acceptable salts with pharmaceutically-acceptable bases.

Wetting agents, emulsifiers and lubricants, such as sodium lauryl sulfate and magnesium stearate, as well as coloring agents, release agents, coating agents, sweetening, flavoring and perfuming agents, preservatives and antioxidants may also be present in the compositions.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which may be combined with a carrier material to produce a single dosage form will vary depending upon the host being treated, the particular mode of administration. The amount of active ingredient which may be combined with a carrier material to produce a single dosage form will generally be that amount of the compound which produces a therapeutic effect.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent. The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which may be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which may be used include polymeric substances and waxes. The active ingredient may also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

VI. Delivery Methods and Devices

The pharmaceutical compositions of this invention may also be administered using a variety of pharmaceutical delivery devices may, which may include hypodermic syringes, multichamber syringes, stents, catheters, transcutaneous patches, microneedles, microabraders, and implantable controlled release devices. In one embodiment, a pharmaceutical delivery device contains or is able to be loaded with at least an effective amount of a receptor coupling agent. Such devices may have the ability to reconstitute a lyophilized form of the antibody construct in the device before delivery. In some embodiments, pharmaceutical delivery device contains or is able to be loaded with at least an effective amount of a receptor coupling agent and an effective amount of a chemotherapeutic agent. The device may in some embodiments be able to deliver or administer the receptor coupling agent and chemotherapeutic agent simultaneously. The device may have the ability to mix the antibody construct and chemotherapeutic agent prior to administration with the device. In still other embodiments, the device may be able to administer the agonist antibody construct and chemotherapeutic agent consecutively.

One pharmaceutical delivery device is a multi-chambered syringe capable of mixing two compounds prior to injection, or delivering them sequentially. A typical dual-chamber syringe and a process for automated manufacture of prefilled such syringes is disclosed in Neue Verpackung, No. 3, 1988, p. 50-52; Drugs Made in Germany, Vol. 30, Pag. 136-140 (1987); Pharm. Ind. 46, Nr. 10 (1984) p. 1045-1048 and Pharm. Ind. 46, Nr. 3 (1984) p. 317-318. The syringe type ampoule is a dual chamber device with a front bottle type opening for needle attachment, two pistons and an exterior type by-pass for mixing a lyophilized powder in the front chamber with a reconstitution liquid in the rear chamber. The process described includes the main steps of washing and siliconizing the syringe barrels, insertion of multiple barrels in carrier trays, sterilization, introduction of middle piston through barrel rear end, turning the trays upside down, introduction of the powder solution through the front opening, lyophilization to dry powder, closure of front opening while in the lyophilizing chamber, turning of trays, introduction of the reconstitution liquid through barrel rear end, insertion of rear piston, removal of products from trays and final control and packaging. Ampoules prefilled with the various components may be manufactured for use with the syringes.

In another embodiment, the multichamber syringe is a Lyo-ject system (Vetter Pharma Turm, Yardley, Pa.). The Lyo-Ject allows the user to lyophilize the drug directly in a syringe, which is packaged with the diluent for quick reconstitution and injection. It is described in patents U.S. Pat. Nos. 4,874,381 and 5,080,649.

In other embodiments, the compounds are administered using two separate syringes, catheters, microneedles, or other device capable of accomplishing injection.

The pharmaceutical compositions of this invention may also be administered using microspheres, liposomes, other microparticulate delivery systems or sustained release formulations placed in, near, or otherwise in communication with affected tissues or the bloodstream. Suitable examples of sustained release carriers include semipermeable polymer matrices in the form of shaped articles such as suppositories or microcapsules. Implantable or microcapsular sustained release matrices include polylactides (U.S. Pat. No. 3,773,319; EP 58,481), copolymers of L-glutamic acid and gamma ethyl-L-glutamate (Sidman et al., (1985) *Biopolymers*, 22:547-56); poly(2-hydroxyethyl-methacrylate) or ethylene vinyl acetate (Langer et al., (1981) *J. Biomed. Mater. Res.* 15:167-277; Langer, (1982) *Chem. Tech.*, 12:98-105).

The compositions of this invention will be administered at an effective dose to treat the particular clinical condition addressed. Determination of a preferred pharmaceutical formulation and a therapeutically efficient dose regimen for a given application is well within the skill of the art taking into consideration, for example, the condition and weight of the patient, the extent of desired treatment and the tolerance of the patient for the treatment.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

VII. Therapeutic Methods

Hence, the present invention further provides novel therapeutic methods of treating cancer comprising administering to the subject an effective amount of a pharmaceutical composition, optionally using a delivery device described above. The methods of the present invention may be used to treat any cancer, including but not limited to treating solid tumors. Examples of solid tumors that can be treated by compounds of the present invention, include but are not limited to breast, testicular, lung, ovary, uterine, cervical, pancreatic, non small cell lung (NSCLC), colon, as well as on prostate, gastric, skin, stomach, esophagus and bladder cancer. In certain embodiments, the method comprises parenterally administering an effective amount of a subject pharmaceutical composition to a subject. In one embodiment, the method comprises intraarterial administration of a subject composition to a subject. In other embodiments, the method comprises administering an effective amount of a subject composition directly to the arterial blood supply of a tumor in a subject. In one embodiment, the methods comprises administering an effective amount of a subject composition directly to the arterial blood supply of the cancerous tumor using a catheter. In embodiments where a catheter is used to administer a subject composition, the insertion of the catheter may be guided or observed by fluoroscopy or other method known in the art by which catheter insertion may be observed and/or guided. In another embodiment, the method comprises chemoembolization. For example a chemoembolization method may comprise blocking a vessel feeding the cancerous tumor with a composition comprised of a resin-like material mixed with an oil base (e.g., polyvinyl alcohol in Ethiodol) and one or more chemotherapeutic agents. In still other embodiments, the method comprises systemic administration of a subject composition to a subject.

In general, chemoembolization or direct intraarterial or intravenous injection therapy utilizing pharmaceutical compositions of the present invention is typically performed in a similar manner, regardless of the site. Briefly, angiography (a road map of the blood vessels), or more specifically in certain embodiments, arteriography, of the area to be embolized may be first performed by injecting radiopaque contrast through a catheter inserted into an artery or vein (depending on the site to be embolized or injected) as an X-ray is taken. The catheter may be inserted either percutaneously or by surgery. The blood vessel may be then embolized by refluxing pharmaceutical compositions of the present invention through the catheter, until flow is observed to cease. Occlusion may be confirmed by repeating the angiogram. In embodiments where direct injection is used, the blood vessel is then infused with a pharmaceutical composition of the invention in the desired dose.

Embolization therapy generally results in the distribution of compositions containing inhibitors throughout the interstices of the tumor or vascular mass to be treated. The physical bulk of the embolic particles clogging the arterial lumen results in the occlusion of the blood supply. In addition to this effect, the presence of an anti-angiogenic factor(s) prevents the formation of new blood vessels to supply the tumor or vascular mass, enhancing the devitalizing effect of cutting off the blood supply. Direct intrarterial or intravenous generally results in distribution of compositions containing inhibitors throughout the interstices of the tumor or vascular mass to be treated as well. However, the blood supply is not generally expected to become occluded with this method.

Within one aspect of the present invention, primary and secondary tumors of the liver or other tissues may be treated utilizing embolization or direct intraarterial or intravenous injection therapy. Briefly, a catheter is inserted via the femoral or brachial artery and advanced into the hepatic artery by steering it through the arterial system under fluoroscopic guidance. The catheter is advanced into the hepatic arterial tree as far as necessary to allow complete blockage of the blood vessels supplying the tumor(s), while sparing as many of the arterial branches supplying normal structures as possible. Ideally this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery is embolized by injecting compositions (as described above) through the arterial catheter until flow in the artery to be blocked ceases, preferably even after observation for 5 minutes. Occlusion of the artery may be confirmed by injecting radio-opaque contrast through the catheter and demonstrating by fluoroscopy or X-ray film that the vessel which previously filled with contrast no longer does so. In embodiments where direct injection is used, the artery is infused by injecting compositions (as described above) through the arterial catheter in a desired dose. The same procedure may be repeated with each feeding artery to be occluded.

In most embodiments, the subject pharmaceutical compositions will incorporate the substance or substances to be delivered in an amount sufficient to deliver to a patient a therapeutically effective amount of an incorporated therapeutic agent or other material as part of a prophylactic or therapeutic treatment. The desired concentration of active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art. The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

Dosage may be based on the amount of the composition per kg body weight of the patient. Other amounts will be known to those of skill in the art and readily determined. Alternatively, the dosage of the subject invention may be determined by reference to the plasma concentrations of the composition. For example, the maximum plasma concentration (Cmax) and the area under the plasma concentration-time curve from time 0 to infinity (AUC (0-4)) may be used. Dosages for the present invention include those that produce the above values for Cmax and AUC (0-4) and other dosages resulting in larger or smaller values for those parameters.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present invention, or alternatively other chemotherapeutic agents, may reduce the required dosage for any individual component because the onset and duration of effect of the different components may be complimentary. In such combined therapy, the different active agents may be delivered together or separately, and simultaneously or at different times within the day. Toxicity and therapeutic efficacy of subject compounds may be determined by standard pharmaceutical procedures in cell cultures or experimental animals, e.g., for determining the LD50 and the ED50. Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the ED50 with little or no toxicity. The dosage may vary within this range depending upon the dosage form employed and the route of administration utilized. For agents of the present invention, the therapeutically effective dose may be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

VIII. Combination Therapeutic Use of Receptor Coupling Agents

In some embodiments, the invention further provides for the use of a receptor coupling agent in combination with a chemotherapeutic agent to treat cancer, and/or inhibit tumor growth Likewise, any of a variety of chemotherapeutic agents may be used or tested for use in the methods of the invention. Such chemotherapeutic agents may include anti-metabolic agents, alkylating agents, platinum-based agents, anthracyclines, antibiotic agents, topoisomerase inhibitors, and others. Various forms of the chemotherapeutic agents and/or other biologically active agents may be used. These include, without limitation, such forms as uncharged molecules, molecular complexes, salts, ethers, esters, amides, and the like, which are biologically activated when implanted, injected or otherwise inserted into the tumor.

Chemotherapy drugs which can be used in combination with the receptor coupling agent of the invention or in the form of a conjugate (e.g., immunotoxin) can be divided into several categories based on how they affect specific chemical substances within cancer cells, which cellular activities or processes the drug interferes with, and which specific phases of the cell cycle the drug affects.

In certain embodiments, the chemotherapeutic agent is an agent that disrupts DNA synthesis. In one embodiment, the agent that disrupts DNA synthesis is a nucleoside analog compound. In certain embodiments, the nucleoside analog compound is gemcitabine. In another embodiment, the agent that disrupts DNA synthesis is an anthracycline compound, and in certain embodiments, the anthracycline compound is adriamycin.

In other embodiments, the chemotherapeutic agent is a topoisomerase I inhibitor. In certain embodiments, the topoisomerase I inhibitor is Camptosar.

The chemotherapeutic agent in other embodiments may be an alkylating agent. Alkylating agents work directly on DNA to prevent the cancer cell from reproducing. As a class of drugs, these agents are not phase-specific (in other words, they work in all phases of the cell cycle). Alkylating agents are commonly active against chronic leukemias, non-Hodgkin's lymphoma, Hodgkin's disease, multiple myeloma, and certain cancers of the lung, breast, and ovary. Examples of alkylating agents include busulfan, cisplatin, carboplatin, chlorambucil, cyclophosphamide, ifosfamide, dacarbazine (DTIC), mechlorethamine (nitrogen mustard), and melphalan. In one embodiment, the alkylating agent is a platinum compound, and in certain embodiments may be selected from the group consisting of carboplatin and cisplatin. In certain embodiments, the platinum compound is cisplatin.

In still other embodiments, the chemotherapeutic agent may be a plant alkaloid. In one embodiment, the plant alkaloid is a taxane, and in certain embodiments may be Taxol.

Methods for testing candidate receptor coupling agents in combination with chemotherapeutic agents in order to determine inhibition of a tumor will occur are taught in Applicants' co-pending PCT Application No. PCT/US03/41243, which is hereby incorporated by reference in its entirety.

In another aspect, the present invention features modified antibodies and antibody conjugates, or fragments thereof, conjugated to another therapeutic moiety, such as a cytotoxin, a drug or a radioisotope. The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody.

Exemplary radioisotopes include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. The radionuclides act by producing ionizing radiation which causes multiple strand breaks in nuclear DNA, leading to cell death. The isotopes used to produce therapeutic conjugates typically produce high energy α- or β-particles which have a short path length. Such radionuclides kill cells to which they are in close proximity, for example neoplastic cells to which the conjugate has attached or has entered. They have little or no effect on non-localized cells. Radionuclides are essentially non-immunogenic.

With respect to the use of radiolabeled conjugates in conjunction with the present invention, polypeptides of the invention may be directly labeled (such as through iodination) or may be labeled indirectly through the use of a chelating agent. As used herein, the phrases "indirect labeling" and "indirect labeling approach" both mean that a chelating agent is covalently attached to an antibody and at least one radionuclide is associated with the chelating agent. Such chelating agents are typically referred to as bifunctional chelating agents as they bind both the polypeptide and the radioisotope. Particularly preferred chelating agents comprise 1-isothiocymatobenzyl-3-methyldiothelene triaminepentaacetic acid ("MX-DTPA") and cyclohexyl diethylenetriamine pentaacetic acid ("CHX-DTPA") derivatives. Other chelating agents comprise P-DOTA and EDTA derivatives. Particularly preferred radionuclides for indirect labeling include $^{111}$In and $^{90}$Y.

When conjugated to a cytotoxin, these antibody conjugates are referred to as "immunotoxins." A cytotoxin or cytotoxic agent includes any agent that is detrimental to (e.g., kills) cells or which inhibits their growth. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, tumor-activated prodrugs (e.g., maytansinoids (e.g., DM-1, as described in U.S. Pat. No. 6,441, 163), puromycin and analogs or homologs thereof, dolastatin 10 or analogs thereof (e.g., auristatin E (AE) or monomethylauristatin E (MMAE)). Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), anti-mitotic agents (e.g., vincristine and vinblastine), CC-1065 analogs, clicheamicin derivatives, anthracyclines, vinca alkaloids, etc.), ricin, diptheria toxin, and pseudomonas exotoxin. Other examples of therapeutic cytotoxins that can be conjugated to an antibody of the invention include calicheamicins and duocarmycins.

In a particular embodiment, a human antibody of the invention is conjugated to a maytansinoid, or a derivative thereof, thereby forming an immunotoxin. U.S. Pat. No. 6,441,163 describes methods of conjugating maytansinoids, and derivatives of maytansinoids, to antibodies using disulfide chemistry. Briefly, in one method of making the conjugate, an excess of a maytansinoid compound having a disulfide moiety is mixed with an antibody in an aqueous solution. The reaction is quenched with an excess of amine and the antibody conjugate is purified by gel filtration.

Antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, tetanus toxoid, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. For diagnostic applications, the antibodies may include a moiety (e.g., biotin, fluorescent moieties, radioactive moieties, histidine tag or other peptide tags) for easy isolation or detection. The antibodies may also include a moiety that can prolong their serum half life, for example, a polyethylene glycol (PEG) moiety, and a member of the immunoglobulin super family or fragment thereof (e.g., a portion of human IgG1 heavy chain constant region such as the hinge, CH2 and CH3 legions).

Techniques for conjugating such therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

IX. Kits

The present invention provides kits for treating various cancers. For example, a kit may comprise one or more pharmaceutical composition as described above and optionally instructions for their use. In still other embodiments, the invention provides kits comprising one more pharmaceutical composition and one or more devices for accomplishing administration of such compositions. For example, a subject kit may comprise a pharmaceutical composition and catheter for accomplishing direct intraarterial injection of the composition into a cancerous tumor. In other embodiments, a subject kit may comprise pre-filled ampoules of a receptor coupling agent, optionally formulated as a pharmaceutical, or lyophilized, for use with a delivery device.

This invention is further illustrated by the following examples which should not be construed as limiting. The contents of all references, patents and published patent applications cited throughout this application, as well as the figures and the Sequence Listing, are incorporated herein by reference.

EXAMPLES

Example 1

Efficacy of Multiple Anti-TNF Agonist Agents at Inducing Tumor Cell Death

Multiple anti-TNF receptor antibodies were used simultaneously to induce cell death in colon carcinoma cells to determine if activating two distinct TNF family receptors improved the efficacy of receptor agonist agents. The results show that multiple antibodies were more effective at killing tumor cells in comparison to administration of a single type of anti-TNF antibodies.

Agonist antibodies, 14A2 and CBE11, directed to TNF family receptor TRAIL-R2 and LTβR, respectively, were used in the assay. Monoclonal murine anti-LTβR antibody CBE11 has been described previously in PCT publication WO 96/22788 and U.S. Pat. No. 6,312,691, and humanized CBE11 has been described in WO 02/30986.

Anti-TRAIL-R2 antibodies are well-known within the TNF field, and anti-TRAIL-R2 mAbs similar to 14A2 have been described (Ichikawa, K., et al., (2001) Nat Med 7:954; Chuntharapai, A., et al., (2001) J Immunol 166:4891). To obtain antibody 14A2, briefly, anti-human TRAIL-R2 mAbs were generated by standard hybridoma technology by immunizing mice with human TRAIL-R2-Ig fusion protein. Hybridomas were subsequently screened for binding to the TRAIL-R2 portion. One such anti-TRAIL-R2 hybridoma, 14A2, bound to WiDr colorectal adenocarcinoma cells in a FACS analysis. 14A2 was identified as a mAb that could induce tumor cell death when immobilized on the plastic surface via an anti-murine Ig Fc domain capture antibody (see filled-in squares, FIG. 1b).

To determine the combined effect of activating TNF receptors TRAIL-R2 and LTβR, colon carcinoma WiDr cells were exposed to soluble murine antibodies CEB11 alone, 14A2 alone, and CBE11 and 14A2 in combination. WiDr cells were used in a four-day MTT assay with 80 U/ml IFNγ. When WiDr cells were cultured with anti-LTβR mAb CBE11 (Browning, J. L., et al., (1996) J Exp Med 183:867) or 14A2 added to the culture media, relatively limited inhibition of cell growth was observed. However, the combination of anti-TNF receptor murine antibodies CBE11 and 14A2 was more effective, as shown in FIG. 2a Likewise, anti-CBE11 was able to potentiate TNF activity in similar assays (Mackay, F., et al., (1997) J Immunol 159:3299). Thus, the combination of murine antibodies CBE11 and 14A2 at activating two TNF family receptors simultaneously was more effective at killing tumor cells than the antibodies alone.

Example 2

Construction of Bispecific TNF-Receptor Coupling Agent

In order to determine whether a coupling agent which activates at least two distinct TNF receptors has improved efficacy over individual activating moieties, a receptor coupling agent in the form of a bispecific multivalent antibody which binds two distinct TNF family receptors, e.g., TRAIL-R2 and LTβR, was created. The bispecific multivalent antibody was constructed containing CBE11 and 14A2 epitope binding domains.

The anti-hu TRAILR2/anti-hu LTβR bispecific antibody (designated LT-BS1) was constructed as follows. The antibody variable regions of the heavy and light 14A2 immunoglobulin chains were determined by PCR using the 14A2 hybridoma. The variable regions were then combined with a constant human light chain region to form a complete chimeric mouse-human 14A2 light chain. The chimeric 14A2 light chain was constructed using the variable domain of a murine lambda light chain, fused to a human kappa constant domain. The lambda-kappa light chain was then used in the construction of the bispecific antibody. The heavy chain variable region was combined with the nonvariable region of the human IgG1 heavy chain with the C-terminal Fv fragment of CBE11. The construction of single chain Fv versions of humanized CBE11 has been previously described in PCT/US03/41393 (WO 04/058191). Thus, the Hercules LT-BS1 heavy chain contains the anti-huTRAILR2 14A2-huIgG1 heavy chain (SEQ ID NO: 1 and 2) with the engineered huCBE11 scFv fused to its C-terminus, while the Hercules light chain is the chimeric 14A2-hu kappa light chain (SEQ ID NO: 3 and 4). A schematic representation of the LT-BS1 Hercules construct is shown in FIG. 9. The nucleotide and amino acid sequence of the LT-BS1 antibody construct are shown in SEQ ID NOs: 5-8.

Co-expression of the heavy and light chain in CHO cells resulted in production of the 14A2/CBE11 bispecific molecules called LT-BS1 here for simplicity (LTβR/TRA1N-R2 bispecific-1). LT-BS1 was purified from the culture supernatant Protein A affinity chromatography. There were no detectable aggregates by size exclusion chromatography.

Example 3

Efficacy of Bispecific TNF-Receptor Coupling Agent at Inducing Tumor Cell Death

Figure 1A:
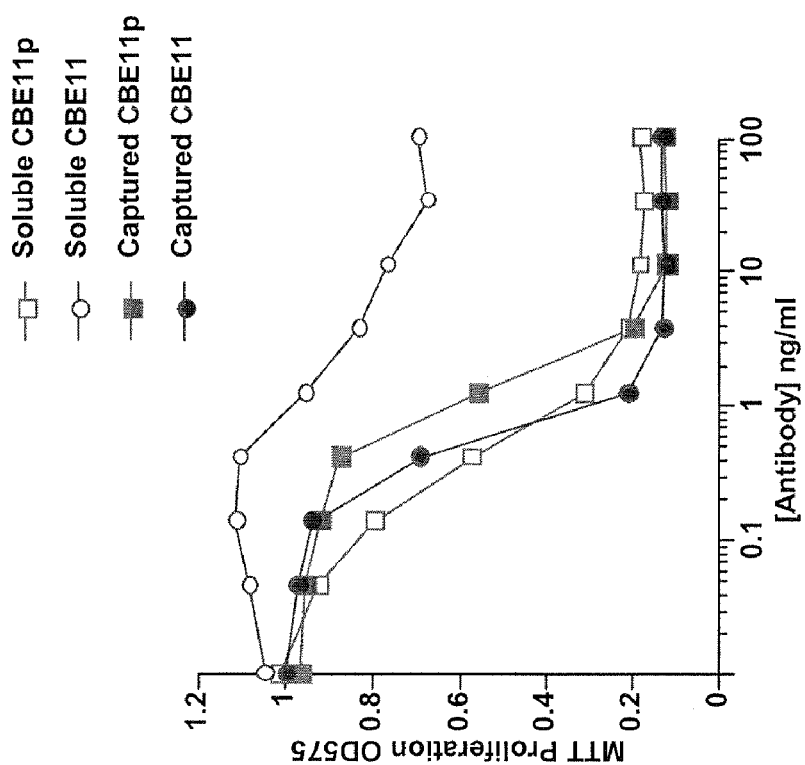

As shown in FIG. 1, both the original murine 14A2 and CBE11 mAbs when immobilized (captured) on plastic, could inhibit HT29 cell growth. However, both antibodies in solution exhibited only weak efficacy. When combined together as two separate mAbs, the simultaneous activation of LTβR and TRAIL-R2 enhanced growth inhibiting activity, as shown in FIG. 2a. Thus, there was increased potency achieved by combining antibodies to two different TNF family receptors.

Figure 2B:
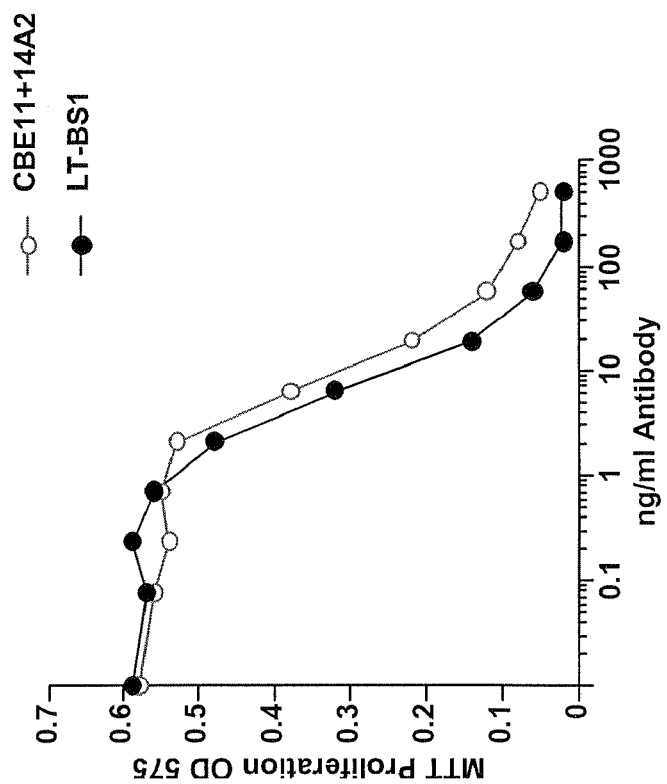
FIGS. 2a-b graphically depict results from a 4-day MTT growth assay in WiDr colon carcinoma cells. Results demonstrate that the bispecific LTβR/TRAIL-R2 antibody (LT-BS1) has more cell death activity (FIG. 2b) than individual parent antibodies CBE11 and 14A2 (FIG. 2a).
Figure 2A:
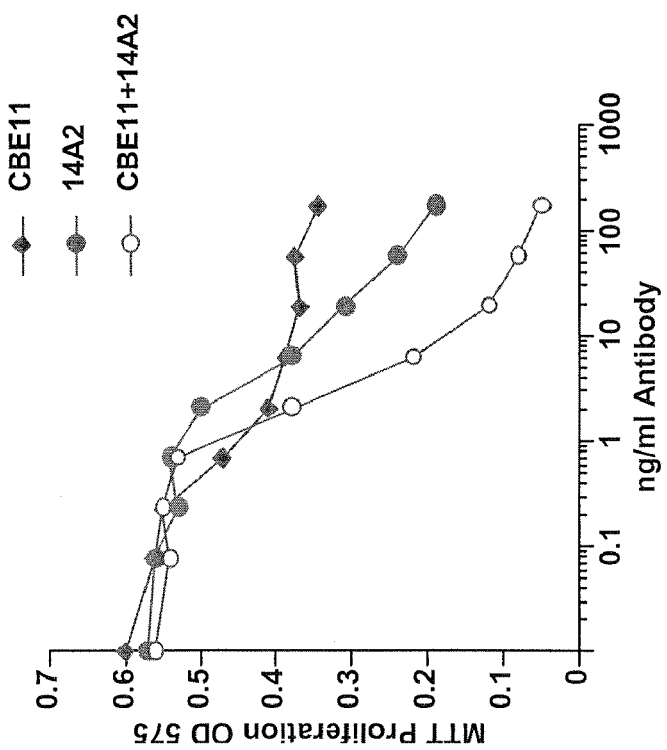

The LT-BS1 construct was as potent as the combination of the two individual mAbs, as shown in FIG. 2b. The LT-BS1 construct demonstrated that the two mAbs are still active when combined into one molecular entity and illustrates the principle of combining anti-receptor mAbs to two different TNF family members for increased benefit.

Figure 3:
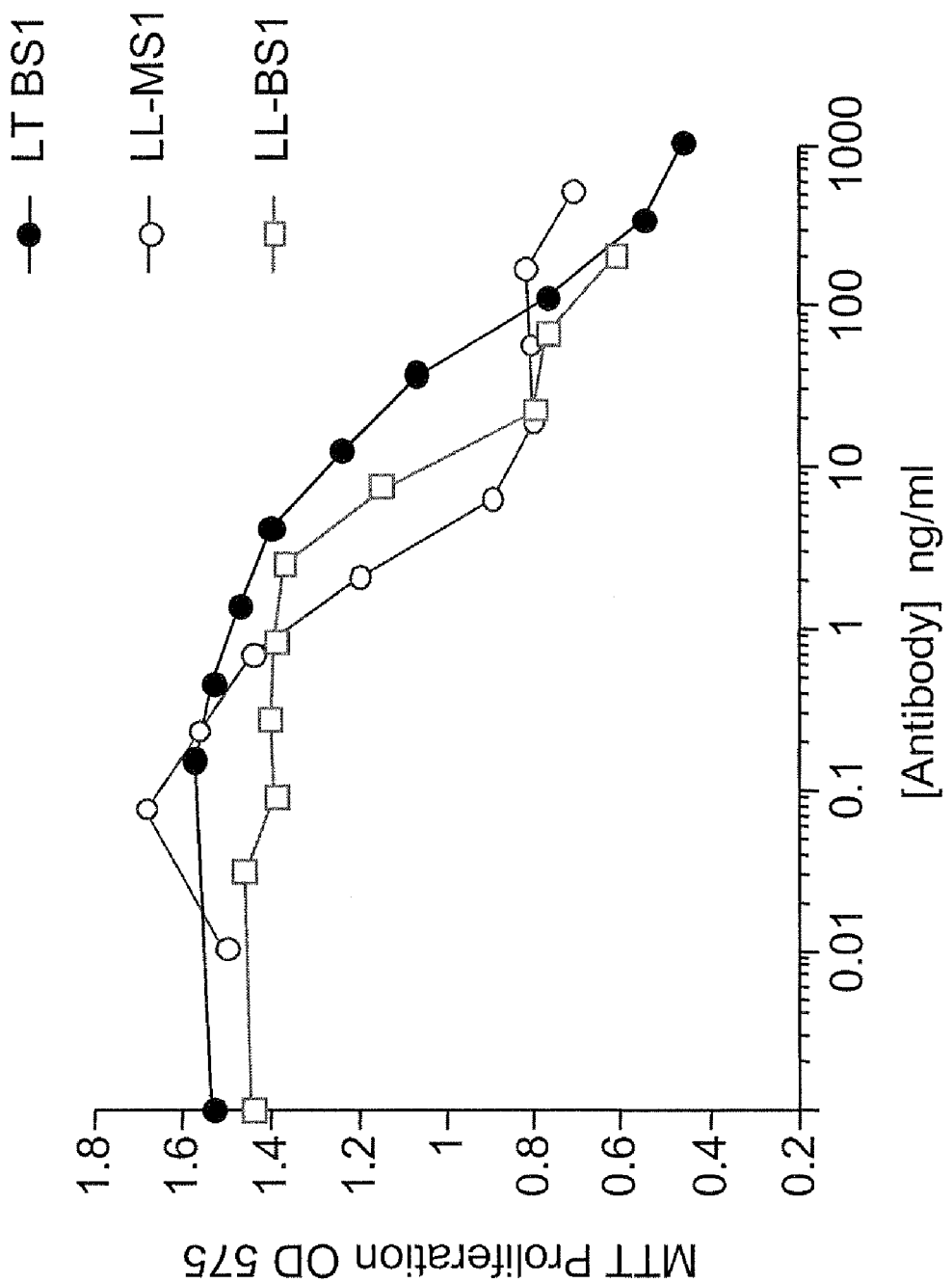
FIG. 3 graphically depicts results from a 4-day MTT growth assay with 80 U/ml of IFNγ in WiDr colon carcinoma cells, comparing the LTβR/TRAIL-R2 bispecific antibody (LT-BS1) to tetravalent LTβR bispecific antibodies LL-BS1 (antibody CBE11 and BHA10) and LL-MS1 (antibody CBE11).

To further examine the potency of the bispecific LT-BS1 antibody, purified LT-BS1 was used in HT29 or WiDr 3-4 day proliferation assays according to standard protocols. WiDr is an HT29 variant line with similar behavior. LT-BS1 was tested in WiDr cells in parallel with multivalent antibodies directed to LTβR. The anti-LTβR antibodies used were LL-MS1 (a monospecific antibody containing CBE11 antigen recognition sites) and LL-BS1 (a bispecific antibody containing CBE11 and BHA10 antigen recognition sites). Descriptions and sequences of the LL-MS1 and LL-BS1 constructs are described in Applicant's co-pending PCT application WO 04/058191, incorporated by reference herein. As shown in FIG. 3, LT-BS1 was able to induce cell death in WiDr colon carcinoma cells, demonstrating potency in colon carcinoma cells comparable to that of the LL-MS1 and LL-BS1 constructs.

Figures 4A, 4B:
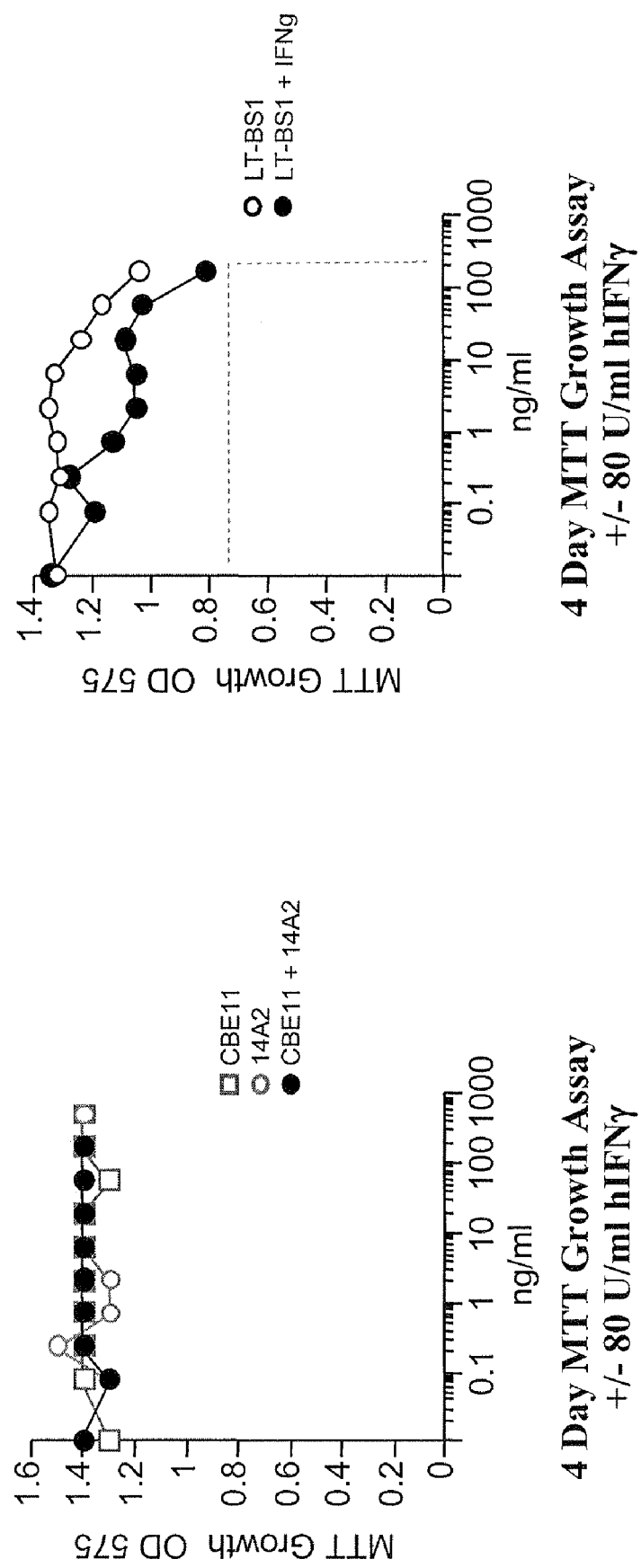
FIGS. 4a-b graphically depict results from a 4-day MTT growth assay with and without 80 U/ml of IFNγ in LS174T tumor cells. The results show the efficacy of receptor coupling agent LT-BS1 and antibodies 14A2 and CBE11 at inhibiting colon carcinoma cell growth (LS174T tumor cells).

Interestingly, in contrast to proliferation experiments in the WiDr colon carcinoma cell line, where similar results were obtained comparing LT-BS1 and the CBE11/14A2 combination, LT-BS1 was more effective than the CBE11/14A2 combination at inducing cell death in the LS174T colon carcinoma cell line. As shown in FIG. 4, the combination of murine CBE11 and 14A2 alone had little effect on cell death, whereas exposure to LT-BS1 or LT-BS1 in combination with IFNγ resulted in a marked decrease in cell viability.

The improved potency of LT-BS1 over the combination of two separate murine mAbs was further examined using various tumor cell lines, as shown in Table 1 and FIGS. 5-8. Proliferation assays were performed in the presence and absence of 80 U/ml IFNγ using soluble antibody according to standard four day MTT growth assay protocols. A range of tumor types were surveyed, including cervical and breast tumor cell lines.

The results demonstrate that LT-BS1 was effective against a wider range of tumors than the parent mAbs CBE11 and 14A2 alone or in combination. The activity of LT-BS1 was dependent on the presence of IFNγ in some cell lines, such as the HT29 and WiDR tumor lines, as is typical of TNF family receptor activation with this cell type. However, efficacy against some tumor types was not dependent on IFNγ addition. The requirement for IFNγ even with WiDr/HT29 is not absolute, for example, good anti-tumor efficacy was observed with anti-LTBR mAb in HT29 in in vivo xenograph tumor models in the complete absence of exogenous IFNγ (Browning et al. (1996) *J. Exp. Med.* 183:867). The enhanced spectrum of anti-tumor activity of LT-BS1 demonstrates the principle that various combinations of TNF-family receptors can have unique activity. This enhanced activity would not be predicted by the activity of the individual parental mAbs.

TABLE 1

| Tumor Line | Type | Sensitivity in a 4-day MTT Growth Assay | | | | | | |
|---|---|---|---|---|---|---|---|---|
| | | CBE11 + IFNg | 14A2 + IFNg | CBE11 + 14A2 + IFNg | LT-BS1 + IFNg | LT-BS1 No IFNg | LL-BS1 + IFNg | CBE11p + IFNg |
| WiDr | Colorectal | + | + | +++ | +++ | - | ++++ | ++++ |
| HT29 | Colorectal | + | + | ++ | +++ | - | nd | ++++ |
| KM20L2 | Colorectal | nd | nd | +++ | +++ | nd | +++ | +++ |
| LS174T | Colorectal | - | - | - | +++ | + | - | +/- |
| CACO-2 | Colorectal | nd | nd | nd | +/- | nd | nd | +/- |
| MCF7 | Breast | - | - | - | ++ | nd | nd | - |
| MDA231 | Breast | - | - | - | +++ | +++ | | - |
| Hela | Cervical | - | - | - | +/- | +/- | | - |
| ME180 | Cervical | +/- | +/- | +/- | ++++ | ++ | nd | +/- |
| A375 | Melanoma | nd | nd | nd | - | nd | nd | - |
| RD | Rhabdomyosarcoma | nd | nd | nd | +/- | nd | nd | +/- |
| SAOS-2 | sarcoma | nd | nd | nd | - | nd | nd | - |
| 293E | normal fibroblast | nd | nd | nd | - | nd | nd | - |
| WI-38 | normal fibroblast | nd | nd | nd | - | nd | nd | - |

Figure 5B:
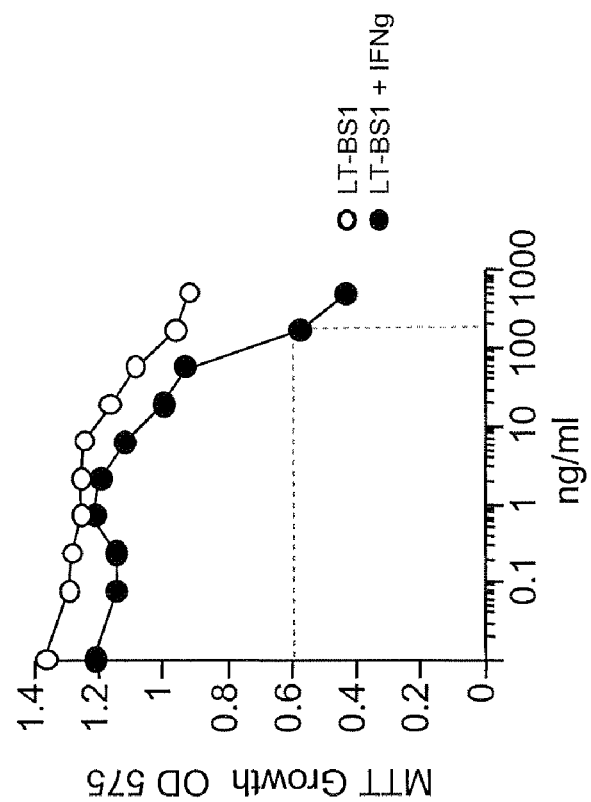
FIGS. 5a-b graphically depict results from a 4-day MTT growth assay with and without 80 U/ml of IFNγ in ME180 tumor cells. The results demonstrate the efficacy of receptor coupling agent LT-BS1 and antibodies 14A2 and CBE11 at inhibiting cervical carcinoma cell growth (ME180 tumor cells).
Figure 5A:
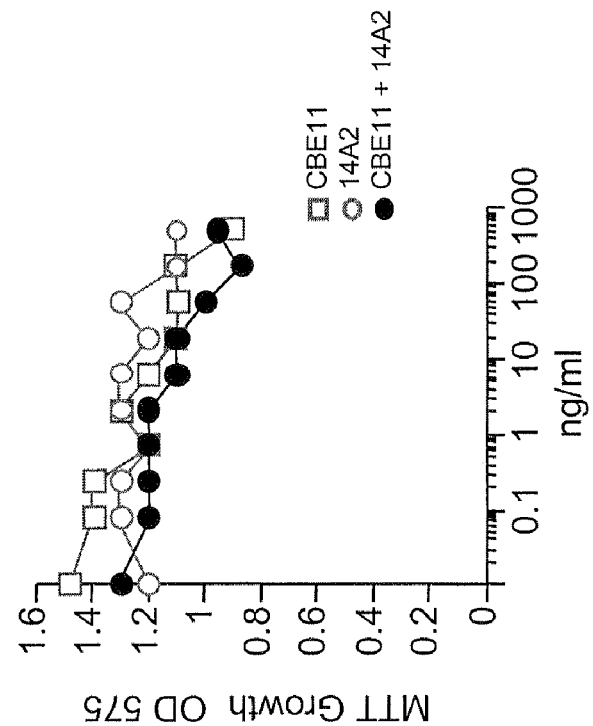
Figures 6A, 6B:
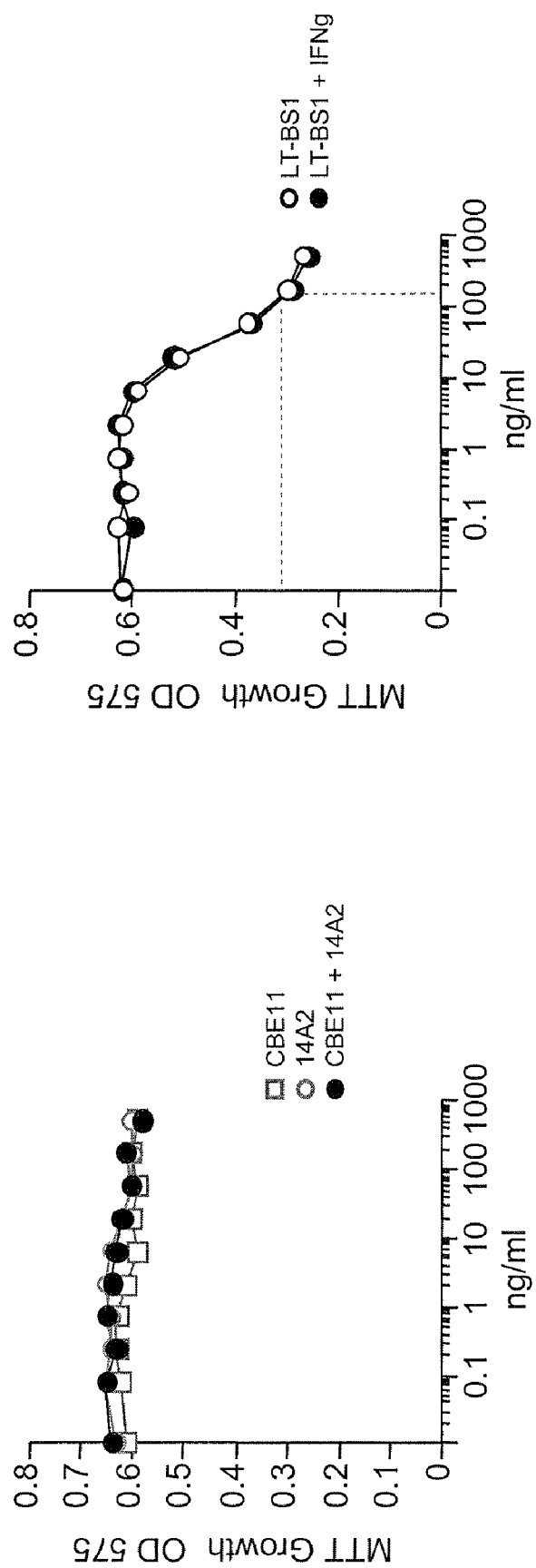
FIGS. 6a-b graphically depict results from a 4-day MTT growth assay with and without 80 U/ml of IFNγ in MDA213 tumor cells. The results show the efficacy of receptor coupling agent LT-BS1 and antibodies 14A2 and CBE11 at inhibiting breast carcinoma cell growth (MDA231 tumor cells).

Shading indicates cells that responded to LT-BS1 without any substantial response to CBE11p or other combos
++++, ++, + scoring refers to the extent of death achieved without a major concentration dependence
CBE11    Anti-LTBR (murine)
CBE11p   Pentameric Version
LL-BS1   Bispecific anti-LTBR
14A2     Anti-TRAIL-R2 (murine)
LT-BS1   LTBR/TRAIL-R2 bispecific ME180 and MDA231 represent cervical and breast tumor cell lines that exhibit a different pattern of responsiveness. Both tumor cell lines did not respond to either CBE11 or 14A2 mAbs alone or the strong LTR agonist pentameric CBE11 (CBE11p); however, the bispecific LT-BS1 was very effective in reducing their growth in in vitro cultures, as shown in FIGS. 5 (ME180 cervical cell line) and 6 (MDA321 breast carcinoma cell line). LT-BS1 activity was enhanced with IFNγ in the ME180 cervical cell line, while potency in the breast carcinoma cell line MDA231 was not effected by the presence of IFN.

Figure 7B:
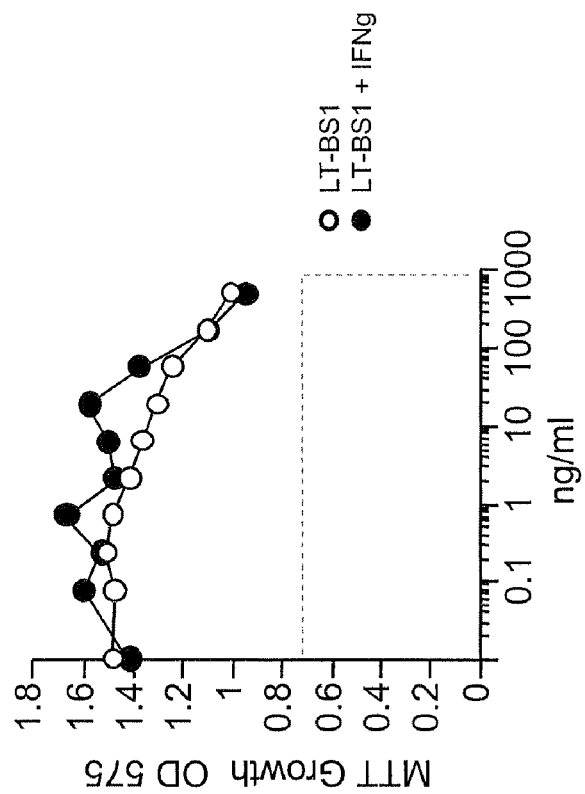
FIGS. 7a-b graphically depict results from a 4-day MTT growth assay with and without 80 U/ml of IFNγ in Hela tumor cells. The results demonstrate the efficacy of receptor coupling agent LT-BS1 and individual antibodies 14A2 and CBE11 at inhibiting Hela cervical carcinoma cell growth.
Figure 7A:
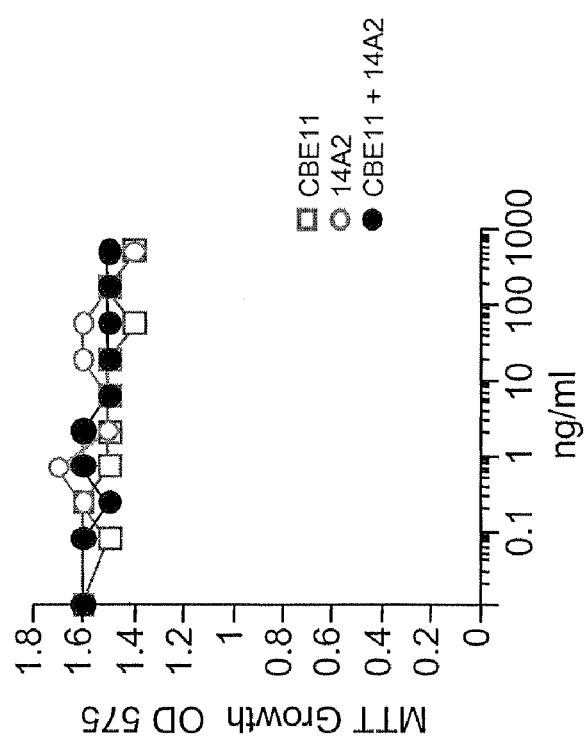

Hela cervical cell carcinoma cells were also assayed, as shown in FIG. 7. Using Hela cells, the LT-BS1 construct proved to be more potent at inducing cell death than murine CBE11 and 14A2 alone or in combination.

A comparison of the different types of cells lines and the efficacy of LT-BS1 in each in comparison to a pentameric version of CBE11 (CBE11p, as described in PCT Application No. PCT/US03/41393, WO 04/058191) is shown in FIG. 8. In sum, LT-BS1 was much more potent than CBE11p.

Based on the results described above, the bispecific construct LT-BS1 was more effective at inducing cell death in tumor cells than introducing each antibody alone in combination. Since dimerization of either receptor was inefficient, the bispecific construct may lead to a novel signal transduction event and/or alter the location of one of the receptors to make signaling more effective. The improved efficacy of the bispecific LT-BS1 construct indicates that a novel event was induced.

The increased potency of LT-BS1 over the individual mAbs, 14A2 and CBE11, could result from the mechanisms described above, i.e. assembly of novel signal transduction complexes or altered localization of the receptors. Another potential mechanism could stem from oligomerization/aggregation of LT-BS1 and as such it resembles the CBE11 pentameric form that has increased efficacy (with sensitive cells) or an oligomeric 14A2 anti-TRAIL-R2 mAb. Biochemical analysis of the purified LT-BS1 showed that it had no detectable higher molecular weight forms both fresh from the freezer or after 5 months at 4 C.

Example 4

Crosslinking TNF-Receptors

To demonstrate that crosslinking between the two receptors, i.e., engaging both receptors using a receptor coupling agent, enhances activity, receptor-immunoglobulin (Ig) fusion proteins were pre-mixed with the receptor coupling agent LT-BS1 to determine if the receptor-Ig fusions could block LT-BS1 activity. It was predicted that pre-mixing either LTBR-Ig or TRAIL-R2-Ig with LT-BS1 to neutralize one side of the construct should block activity in a similar manner. The experiment was performed with three tumor lines, WiDr, ME180 and MDA231. In all three cases, both receptor-Ig fusions (LTβR or TRAIL-R2) were effective blockers of LT-BS1 activity. Furthermore, the single mAbs in solution were inactive (only soluble CBE11 had relatively weak activity against WiDr as was the basis for selecting this mAb for clinical work). This experiment indicates that crosslinking two TNF receptors with a receptor coupling agent provides for enhanced activity.

Example 5

Design and Testing of Additional TNF-Family Receptor Pairs

Another example of a coupling receptor agent is an agent directed the human Fn14 receptor, which is the receptor to TWEAK. Antibodies against the human Fn14 receptor are prepared by immunization of wild type mice, or Fn14 receptor deficient mice or other species with recombinant Fn14-Fc fusion protein or soluble Fn14. Hybridomas are prepared by conventional methods and screened for Fn14 binding.

Agonistic TNF mAbs are identified by analysis of NFkB activation. In the case of Fn14, NFkB activation leads to release of IL-8 or other chemokines, which forms a simple cell based screening method. To determine whether an antibody is agonistic, monoclonals are added into solution or immobilized on plastic. Upon addition of the antibody, release of a chemokine indicates receptor activation. Alternatively, a range of reporter cell lines are now available commercially or easily constructed to monitor NFkB activation. Another alternative to determine whether an antibody activates includes cell proliferation and cell death and caspase activation assays, commonly employed to test for induction of death programs.

Once the agonistic antibody is identified through standard screening techniques, the RNA encoding the Ig molecules is sequenced and recombinant forms of these mAbs can be designed. CBE11 scFv construct is added to the C terminus of the agonistic Fn14 mAb sequence and bispecific forms of such an anti-Fn14-anti-LTBR combination are expressed and isolated by protein A chromatography. Either the original murine Fc is used or the original anti-Fn14 mAb is converted to a chimeric mAb with a human IgG Fc domain. Alternatively, an agonistic anti-Fn14 scFv is designed and added to the chimeric versions of anti-LTBR, e.g. CBE11.

Once bispecific antibodies are constructed which are directed to two distinct TNF receptors, such as Fn14 and LTBR, the resultant proteins are tested in vitro for activity on tumor lines that express both receptors. Additive or synergistic activity are confirmed using in vivo testing of the bispecific with that tumor in a xenograft setting. Human tumor databases are screened to determine if such receptor pairings occur with a reasonable frequency, i.e. greater than 5-30% in the population. Active molecules as defined above targeted at tumors with a reasonable frequency are candidates for human testing.

Example 6

Selecting Potential TNF-Family Receptor Pairs for Tumor Therapy

Existing public gene expression databases are queried to find those receptors that are expressed on a particular tumor type, e.g. ductal invasive breast carcinomas. Tumor specific pairs of receptors, e.g. LTβR and RANK, are chosen and those that are not abundantly expressed in critical cell types such as microvasculature and hepatocytes are of lower priority.

In vitro assays are used to further validate the prediction process. For example, the LT-BS1 construct can kill a tumor cell such as MDA231 as defined above. In another example, LT-BS1 is added to cultures of primary endothelial cells and evidence of endothelial activation is then examined in several ways. First, chemokine release from these cells is studied because it serves as an indicator of signaling capability. Pro-inflammatory activation of endothelial cells involves the induced display of various adhesion molecules that promotes leucocyte adhesion and trafficking. E-selectin, VCAM and ICAM are such molecules and their induction is followed by FACS analysis (see, for example, Hochmna et al. (1995) *J. Inflammation* 46:220). It is likely that LT-BS1 does not efficiently activate endothelial cells. In contrast, TNF is a strong pro-inflammatory signal and it upregulates the expression of all three of these molecules. Gene expression analyses using chip technology is also be exploited to obtain a more detailed picture of whether these novel bispecific antibodies have unusual and potentially detrimental consequences. Endothelial activation and endothelial or hepatocyte cell death are negative indicators.

By using profiling to find unique tumor-oriented receptor combinations coupled with favorable predictions for reduced expression on endothelial cells and hepatocytes, one optimizes the selection process. The selections are validated by use of in vitro tumor growth assays as well as endothelial activation and survival assays.

Equivalents

One of ordinary skill in the art will recognize that many variations and changes may be made to the invention as described in the Detailed Description without departing from the spirit and scope of the invention. The examples provided herein are merely illustrative, and should not be construed as limiting of the scope of the invention, which is set forth in the appended claims.

All publications and patents mentioned herein are hereby incorporated by reference in their entirety as if each individual publication or patent was specifically and individually indicated to be incorporated by reference.

What is claimed:

1. A method of decreasing tumor volume comprising administering to a subject an effective amount of a receptor coupling agent comprising at least two components which specifically crosslinks at least two distinct TNF family receptor types, and induces formation of heteromeric TNF receptor complexes, wherein the receptor coupling agent comprises a first binding specificity directed to TRAIL-R2, and a second binding specificity directed to Lymphotoxin-β-Receptor (LTβR), and wherein the first and second binding specificities are conferred by a component selected from the group consisting of an antibody, an antigen binding fragment thereof, an scFv molecule, and a ligand to the TNF receptor, and wherein the tumor is a solid tumor.

2. The method of claim 1, wherein the receptor coupling agent is administered in the presence of IFNγ.

3. The method of claim 1, wherein the receptor coupling agent is administered in the presence of a chemotherapeutic agent.

4. A method of reducing tumor burden comprising administering to a subject an effective amount of a receptor coupling agent comprising at least two components which specifically crosslinks at least two distinct TNF family receptor types, and induces formation of heteromeric TNF receptor complexes, wherein the receptor coupling agent comprises a first binding specificity directed to TRAIL-R2, and a second binding specificity directed to Lymphotoxin-β-Receptor (LTβR), and wherein the first and second binding specificities are conferred by a component selected from the group consisting of an antibody, an antigen binding fragment thereof, an scFv molecule, and a ligand to the TNF receptor, and wherein the cancer is a solid tumor.

5. The method of claim 4, wherein the receptor coupling agent is administered in the presence of IFNγ.

6. The method of claim 4, wherein the receptor coupling agent is administered in the presence of a chemotherapeutic agent.

7. The method of claim 1 or 4, wherein the first or second binding specificity is conferred by an antibody or antigen binding fragment thereof.

8. The method of claim 1 or 4, wherein at least the first or second binding specificity is conferred by a single chain Fv fragment.

9. The method of claim 1 or 4, wherein the first or second binding specificity is conferred by a natural ligand for the receptor and the remaining binding specificity is conferred by an antibody, or an antigen binding fragment thereof.

10. The method of claim 1 or 4, wherein at least one of the TNF receptors is overexpressed on tumor cells.

11. The method of claim 10, wherein at least one of the TNF receptors is not overexpressed on normal liver or endothelial cells.

12. The method of claim 1 or 4, wherein the second binding specificity is conferred by an anti-LTβ receptor (LTβR) antibody, or antigen binding fragment thereof.

13. The method of claim 12, wherein the anti-LTβR antibody, or antigen binding fragment thereof is derived from a humanized CBE11 antibody.

14. The method of claim 12, wherein the first binding specificity is conferred by an anti- TRAIL-R2 antibody, or antigen binding fragment thereof.

15. The method of claim 14, wherein the anti-TRAIL-R2 antibody, or antigen binding fragment thereof is derived from a humanized 14A2 antibody.

16. The method of claim 1 or 4, wherein the second binding specificity is conferred by a humanized CBE11 antibody or antigen binding fragment thereof, and the first binding specificity is conferred by a humanized 14A2 antibody or antigen binding fragment thereof.

17. The method of claim 1 or 4, wherein the first or second binding specificity is conferred by at least two trimeric ligand-Fc constructs and the remaining binding specificity is conferred by three antibodies.

18. The method of claim 1 or 4, wherein at least one of the TNF family receptors is not normally found in a raft environment on the cell surface.

19. The method of claim 1 or 4, wherein at least one of the TNF family receptors is normally found in a raft environment on the cell surface.

20. A method of decreasing tumor volume comprising administering to a subject an effective amount of a bispecific antibody comprising a first and a second binding specificity and at least four antigen binding sites, which bispecific antibody induces formation of a heteromeric receptor complex, said bispecific antibody comprising a first binding specificity directed to TRAIL-R2, and a second binding specificity directed to LTβR.

21. The method of claim 20, wherein the second binding specificity is derived from a anti-LTβR antibody, antigen binding fragment thereof, or an scFv molecule.

22. The method of claim 21, wherein the anti-LTβR antibody, antigen binding fragment thereof, or scFv molecule is derived from a humanized CBE11 antibody.

23. The method of claim 20, wherein the first binding specificity is derived from an anti- TRAIL-R2 antibody, antigen binding fragment thereof, or an scFv molecule.

24. The method of claim 23, wherein the anti-TRAIL-R2 antibody,-antigen binding fragment thereof, or scFv molecule is derived from a humanized 14A2 antibody.

25. A method of decreasing tumor volume comprising administering to a subject an effective amount of an antibody comprising at least a first and a second binding specificity and at least four antigen binding sites, which antibody crosslinks at least two distinct TNF family receptors and induces formation of a heteromeric receptor complex, the antibody comprising a first binding specificity directed to LTBR and a second binding specificity directed to TRAIL-R2.

26. The method of claim 25, wherein the LTBR binding specificity is provided by an antibody or a single chain variable region.

27. The method of claim 25, wherein the LTBR binding specificity is provided by an antigen binding fragment of an antibody, wherein the antigen binding fragment is selected from the group comprising a Fab fragment, a F(ab)$_2$ fragment, and a F$_v$ fragment.

28. The method of claim 25, wherein the LTBR binding specificity is provided by a ligand.

29. The method of claim 25, wherein the TRAIL-R2 binding specificity is provided by an antibody or a single chain variable region.

30. The method of claim 25, wherein the TRAIL-R2 binding specificity is provided by an antigen binding fragment of an antibody, wherein the antigen binding fragment is selected from the group comprising a Fab fragment, a F(ab)$_2$ fragment, and a F$_v$ fragment.

31. The method of claim 25, wherein the TRAIL-R2 binding specificity is provided by a ligand.

32. The method of claim 25, wherein the antibody comprises a heavy chain comprising an amino acid sequence set forth as SEQ ID NO: 6 and a light chain comprising an amino acid sequence set forth as SEQ ID NO: 8.

* * * * *

SEQUENCE LISTING

<160> NUMBER OF SEQ ID NOS: 8

<210> SEQ ID NO 1
<211> LENGTH: 1350
<212> TYPE: DNA
<213> ORGANISM: Artificial Sequence
<220> FEATURE:
<223> OTHER INFORMATION: Description of Artificial Sequence: DNA
      sequence of mature chimeric 14A2-huIgG1 heavy chain

<400> SEQUENCE: 1

```
cagatccagt tggtgcagtc tggacctgag ctgaagaagc tggagagac agtcaagatc      60
tcctgcaagg cttctggttt taccttcaca gactattcaa tacactgggt gaaacaggct     120
ccaggaaagg gtttaaagtg gatgggctgg ataaacactg agactggtga gccaacatat     180
acagatgact tcaagggacg atttgccttc tctttggtga cctctgccac cactgcctat     240
ttgcagatca caacctcaa caatgaggac acggctacat ttttctgtgc tagattcatc     300
tatgatcctt attgggggtt tgcttactgg ggccagggga ctctggtcac tgtctccgca    360
gccagcacga agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgtg acaagactca cacatgccca ccgtgcccag cacctgaact cctggggggga   720
ccgtcagtct tcctcttccc cccaaaaccc aaggacaccc tcatgatctc ccggaccct     780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcccagccc ccatcgagaa aaccatctcc    1020
aaagccaaag gcagccccg agaaccacag gtgtacaccc tgccccccatc cgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg    1200
ttggactccg acggctcctt cttcctctac agcaagctca ccgtggacaa gagcaggtgg    1260
cagcagggga acgtcttctc atgctccgtg atgcatgagg ctctgcacaa ccactacacg    1320
cagaagagcc tctccctgtc tccgggttga                                     1350
```

<210> SEQ ID NO 2
<211> LENGTH: 449
<212> TYPE: PRT
<213> ORGANISM: Artificial Sequence
<220> FEATURE:
<223> OTHER INFORMATION: Description of Artificial Sequence: Protein
      sequence of mature chimeric 14A2-huIgG1 heavy
      chain

<400> SEQUENCE: 2

Gln Ile Gln Leu Val Gln Ser Gly Pro Glu Leu Lys Lys Pro Gly Glu

```
              1               5              10              15
Thr Val Lys Ile Ser Cys Lys Ala Ser Gly Phe Thr Phe Thr Asp Tyr
                 20                  25                  30

Ser Ile His Trp Val Lys Gln Ala Pro Gly Lys Gly Leu Lys Trp Met
                 35                  40                  45

Gly Trp Ile Asn Thr Glu Thr Gly Glu Pro Thr Tyr Thr Asp Asp Phe
 50                  55                  60

Lys Gly Arg Phe Ala Phe Ser Leu Val Thr Ser Ala Thr Thr Ala Tyr
 65                  70                  75                  80

Leu Gln Ile Asn Asn Leu Asn Asn Glu Asp Thr Ala Thr Phe Phe Cys
                 85                  90                  95

Ala Arg Phe Ile Tyr Asp Pro Tyr Trp Gly Phe Ala Tyr Trp Gly Gln
                100                 105                 110

Gly Thr Leu Val Thr Val Ser Ala Ala Ser Thr Lys Gly Pro Ser Val
                115                 120                 125

Phe Pro Leu Ala Pro Ser Ser Lys Ser Thr Ser Gly Gly Thr Ala Ala
                130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
                210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
                275                 280                 285

Asn Ala Lys Thr Lys Pro Arg Glu Glu Gln Tyr Asn Ser Thr Tyr Arg
                290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430
```

```
Glu Ala Leu His Asn His Tyr Thr Gln Lys Ser Leu Ser Leu Ser Pro
        435                 440                 445

Gly

<210> SEQ ID NO 3
<211> LENGTH: 669
<212> TYPE: DNA
<213> ORGANISM: Artificial Sequence
<220> FEATURE:
<223> OTHER INFORMATION: Description of Artificial Sequence: DNA
      sequence of mature chimeric 14A2-human kappa light chain

<400> SEQUENCE: 3
caacttgtgc tcactcagtc atcttcagtc tctttctccc tgggagcctc agcaaaactc      60
acgtgcacct tgagtagtca gcacagtacg tacaccattg aatggtatca gcaacagccc     120
ctcaagcctc ctaagtatgt gatggagctt aagaaagatg gaagccacag cacaggtgat     180
gggattcctg atcgcttctc tggatccagc tctggtgctg atcgctacct tagcatttcc     240
aacatccagc ctgaagatga agcaatatac atctgtggtg tgggtgatac aattaaggaa     300
caatttgtgt atgttttcgg cggtggaacc aaggtcgaaa tcaaacgtac ggtggctgca     360
ccatctgtct tcatcttccc gccatctgat gagcagttga aatctggaac tgcctctgtt     420
gtgtgcctgc tgaataactt ctatcccaga gaggccaaag tacagtggaa ggtggataac     480
gccctccaat cgggtaactc ccaggagagt gtcacagagc aggacagcaa ggacagcacc     540
tacagcctca gcagcaccct gacgctgagc aaagcagact acgagaaaca caaagtctac     600
gcctgcgaag tcacccatca gggcctgagc tcgcccgtca caaagagctt caacagggga     660
gagtgttag                                                             669

<210> SEQ ID NO 4
<211> LENGTH: 222
<212> TYPE: PRT
<213> ORGANISM: Artificial Sequence
<220> FEATURE:
<223> OTHER INFORMATION: Description of Artificial Sequence: Protein
      sequence of mature chimeric 14A2-human kappa light
      chain

<400> SEQUENCE: 4

Gln Leu Val Leu Thr Gln Ser Ser Ser Val Ser Phe Ser Leu Gly Ala
  1               5                  10                  15

Ser Ala Lys Leu Thr Cys Thr Leu Ser Ser Gln His Ser Thr Tyr Thr
                20                  25                  30

Ile Glu Trp Tyr Gln Gln Pro Leu Lys Pro Pro Lys Tyr Val Met
            35                  40                  45

Glu Leu Lys Lys Asp Gly Ser His Ser Thr Gly Asp Gly Ile Pro Asp
 50                  55                  60

Arg Phe Ser Gly Ser Ser Ser Gly Ala Asp Arg Tyr Leu Ser Ile Ser
 65                  70                  75                  80

Asn Ile Gln Pro Glu Asp Glu Ala Ile Tyr Ile Cys Gly Val Gly Asp
                85                  90                  95

Thr Ile Lys Glu Gln Phe Val Tyr Val Phe Gly Gly Gly Thr Lys Val
            100                 105                 110

Glu Ile Lys Arg Thr Val Ala Ala Pro Ser Val Phe Ile Phe Pro Pro
        115                 120                 125

Ser Asp Glu Gln Leu Lys Ser Gly Thr Ala Ser Val Val Cys Leu Leu
    130                 135                 140

Asn Asn Phe Tyr Pro Arg Glu Ala Lys Val Gln Trp Lys Val Asp Asn
```

|     |     |     | 145 |     |     |     | 150 |     |     |     | 155 |     |     |     | 160 |
| --- | --- | --- | --- | --- | --- | --- | --- | --- | --- | --- | --- | --- | --- | --- | --- |
| Ala | Leu | Gln | Ser | Gly | Asn | Ser | Gln | Glu | Ser | Val | Thr | Glu | Gln | Asp | Ser |
|     |     |     |     | 165 |     |     |     |     | 170 |     |     |     |     | 175 |     |
| Lys | Asp | Ser | Thr | Tyr | Ser | Leu | Ser | Ser | Thr | Leu | Thr | Leu | Ser | Lys | Ala |
|     |     |     | 180 |     |     |     |     |     | 185 |     |     |     | 190 |     |     |
| Asp | Tyr | Glu | Lys | His | Lys | Val | Tyr | Ala | Cys | Glu | Val | Thr | His | Gln | Gly |
|     |     |     | 195 |     |     |     |     | 200 |     |     |     |     | 205 |     |     |
| Leu | Ser | Ser | Pro | Val | Thr | Lys | Ser | Phe | Asn | Arg | Gly | Glu | Cys |     |     |
|     |     |     | 210 |     |     |     | 215 |     |     |     | 220 |     |     |     |     |

<210> SEQ ID NO 5
<211> LENGTH: 2106
<212> TYPE: DNA
<213> ORGANISM: Artificial Sequence
<220> FEATURE:
<223> OTHER INFORMATION: Description of Artificial Sequence: DNA
      sequence of mature Hercules bispecific antibody heavy chain
      (LT-BS1)

<400> SEQUENCE: 5

| | | |
|---|---|---|
| cagatccagt tggtgcagtc tggacctgag ctgaagaagc ctggagagac agtcaagatc | 60 |
| tcctgcaagg cttctggttt taccttcaca gactattcaa tacactgggt gaaacaggct | 120 |
| ccaggaaagg gtttaaagtg gatgggctgg ataaacactg agactggtga gccaacatat | 180 |
| acagatgact tcaagggacg atttgccttc tctttggtga cctctgccac cactgcctat | 240 |
| ttgcagatca caaccctcaa caatgaggac acggctacat ttttctgtgc tagattcatc | 300 |
| tatgatcctt attgggggt tgcttactgg ggccagggga ctctggtcac tgtctccgca | 360 |
| gccagcacga agggcccatc ggtcttcccc ctggcaccct cctccaagag cacctctggg | 420 |
| ggcacagcgg ccctgggctg cctggtcaag gactacttcc ccgaaccggt gacggtgtcg | 480 |
| tggaactcag gcgccctgac cagcggcgtg cacaccttcc cggctgtcct acagtcctca | 540 |
| ggactctact ccctcagcag cgtggtgacc gtgccctcca gcagcttggg cacccagacc | 600 |
| tacatctgca acgtgaatca caagcccagc aacaccaagg tggacaagaa agttgagccc | 660 |
| aaatcttgtg acaagactca cacatgccca ccgtgcccag cacctgaact cctgggggga | 720 |
| ccgtcagtct tcctcttccc cccaaaaccc aaggacaccc tcatgatctc ccggacccct | 780 |
| gaggtcacat gcgtggtggt ggacgtgagc cacgaagacc ctgaggtcaa gttcaactgg | 840 |
| tacgtggacg gcgtggaggt gcataatgcc aagacaaagc cgcgggagga gcagtacaac | 900 |
| agcacgtacc gtgtggtcag cgtcctcacc gtcctgcacc aggactggct gaatggcaag | 960 |
| gagtacaagt gcaaggtctc caacaaagcc ctcccagccc ccatcgagaa aaccatctcc | 1020 |
| aaagccaaag gcagccccg agaaccacag gtgtacaccc tgcccccatc ccgcgatgag | 1080 |
| ctgaccaaga accaggtcag cctgacctgc ctggtcaaag gcttctatcc cagcgacatc | 1140 |
| gccgtggagt gggagagcaa tgggcagccg gagaacaact acaagaccac gcctcccgtg | 1200 |
| ttggactccg acggctcctt cttcctctac agcaagctca ccgtggacaa gagcaggtgg | 1260 |
| cagcagggga acgtcttctc atgctccgtg atgcatgagg ctctgcacaa ccactacacg | 1320 |
| cagaagagcc tctccctgtc tccgggggg ggaggtggat caggaggtgg cggctccgag | 1380 |
| gtacaactgg tggagtctgg gggaggctta gtgaagcctg agggtccct gaggctctcc | 1440 |
| tgtgcagcct ctggattcac tttcagtgac tattacatgt attggtttcg ccaggcaccg | 1500 |
| ggaaaggggc tggagtgggt cgcaaccatt agtgatggtg gtagttacac ctactatcca | 1560 |
| gacagtgtga aggggcgatt caccatctcc agagacaatg ccaagaacag cctctacctg | 1620 |

-continued

```
cagatgagca gcctgagggc tgaggacaca gctgtgtatt actgcgcaag agaggagaat    1680
ggtaactttt actactttga ctactggggc caagggacca cggtcaccgt ctcctctggg    1740
ggcggggggt ccgggggagg cgggtcggga ggtggcggaa gtgatatcca gatgacccag    1800
tctccatcat ccttgtctgc atcggtggga gacagggtca ctatcacttg caaggcgggt    1860
caggacatta aaagctattt aagctggtac cagcagaaac cagggaaagc gcctaagctt    1920
ctgatctatt atgcaacaag gttggcagat ggggtcccat caagattcag tgcagtggat    1980
tctggtacag attatactct aaccatcagc agcctgcagc ctgaggattt cgcaacttat    2040
tactgtctac agcatggtga gagcccgtgg acgttcggtg aggcaccaa gctggagatc    2100 aaatga                                                              2106
```

<210> SEQ ID NO 6
<211> LENGTH: 701
<212> TYPE: PRT
<213> ORGANISM: Artificial Sequence
<220> FEATURE:
<223> OTHER INFORMATION: Description of Artificial Sequence: Protein of mature Hercules bispecific antibody heavy chain (LT-BS1)

<400> SEQUENCE: 6

```
Gln Ile Gln Leu Val Gln Ser Gly Pro Glu Leu Lys Lys Pro Gly Glu
  1               5                  10                  15

Thr Val Lys Ile Ser Cys Lys Ala Ser Gly Phe Thr Phe Thr Asp Tyr
             20                  25                  30

Ser Ile His Trp Val Lys Gln Ala Pro Gly Lys Gly Leu Lys Trp Met
         35                  40                  45

Gly Trp Ile Asn Thr Glu Thr Gly Glu Pro Thr Tyr Thr Asp Asp Phe
     50                  55                  60

Lys Gly Arg Phe Ala Phe Ser Leu Val Thr Ser Ala Thr Thr Ala Tyr
 65                  70                  75                  80

Leu Gln Ile Asn Asn Leu Asn Asn Glu Asp Thr Ala Thr Phe Phe Cys
                 85                  90                  95

Ala Arg Phe Ile Tyr Asp Pro Tyr Trp Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

-continued

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Gly Gly Gly Gly Ser Gly Gly Gly Gly Ser Glu Val Gln Leu Val
450                 455                 460

Glu Ser Gly Gly Gly Leu Val Lys Pro Gly Gly Ser Leu Arg Leu Ser
465                 470                 475                 480

Cys Ala Ala Ser Gly Phe Thr Phe Ser Asp Tyr Tyr Met Tyr Trp Phe
                485                 490                 495

Arg Gln Ala Pro Gly Lys Gly Leu Glu Trp Val Ala Thr Ile Ser Asp
            500                 505                 510

Gly Gly Ser Tyr Thr Tyr Tyr Pro Asp Ser Val Lys Gly Arg Phe Thr
        515                 520                 525

Ile Ser Arg Asp Asn Ala Lys Asn Ser Leu Tyr Leu Gln Met Ser Ser
530                 535                 540

Leu Arg Ala Glu Asp Thr Ala Val Tyr Tyr Cys Ala Arg Glu Glu Asn
545                 550                 555                 560

Gly Asn Phe Tyr Tyr Phe Asp Tyr Trp Gly Gln Gly Thr Thr Val Thr
                565                 570                 575

Val Ser Ser Gly Gly Gly Gly Ser Gly Gly Gly Gly Ser Gly Gly Gly
            580                 585                 590

Gly Ser Asp Ile Gln Met Thr Gln Ser Pro Ser Ser Leu Ser Ala Ser
        595                 600                 605

Val Gly Asp Arg Val Thr Ile Thr Cys Lys Ala Gly Gln Asp Ile Lys
610                 615                 620

Ser Tyr Leu Ser Trp Tyr Gln Gln Lys Pro Gly Lys Ala Pro Lys Leu
625                 630                 635                 640

Leu Ile Tyr Tyr Ala Thr Arg Leu Ala Asp Gly Val Pro Ser Arg Phe
                645                 650                 655

Ser Gly Ser Gly Ser Gly Thr Asp Tyr Thr Leu Thr Ile Ser Ser Leu
            660                 665                 670

Gln Pro Glu Asp Phe Ala Thr Tyr Tyr Cys Leu Gln His Gly Glu Ser
        675                 680                 685

Pro Trp Thr Phe Gly Gly Gly Thr Lys Leu Glu Ile Lys
690                 695                 700
```

<210> SEQ ID NO 7
<211> LENGTH: 669
<212> TYPE: DNA
<213> ORGANISM: Artificial Sequence
<220> FEATURE:
<223> OTHER INFORMATION: Description of Artificial Sequence: DNA
sequence of mature Hercules bispecific antibody light chain
(LT-BS1)

<400> SEQUENCE: 7

```
caacttgtgc tcactcagtc atcttcagtc tctttctccc tgggagcctc agcaaaactc        60
acgtgcacct tgagtagtca gcacagtacg tacaccattg aatggtatca gcaacagccc       120
ctcaagcctc ctaagtatgt gatggagctt aagaaagatg gaagccacag cacaggtgat       180
gggattcctg atcgcttctc tggatccagc tctggtgctg atcgctacct tagcatttcc       240
aacatccagc ctgaagatga agcaatatac atctgtggtg tgggtgatac aattaaggaa       300
caatttgtgt atgttttcgg cggtggaacc aaggtcgaaa tcaaacgtac ggtggctgca       360
ccatctgtct tcatcttccc gccatctgat gagcagttga atctggaac tgcctctgtt       420 gtgtgcctgc tgaataactt ctatcccaga gaggccaaag tacagtggaa ggtggataac       480
gccctccaat cgggtaactc ccaggagagt gtcacagagc aggacagcaa ggacagcacc       540
tacagcctca gcagcaccct gacgctgagc aaagcagact acgagaaaca caaagtctac       600
gcctgcgaag tcacccatca gggcctgagc tcgcccgtca caaagagctt caacagggga       660
gagtgttag                                                               669
```

<210> SEQ ID NO 8
<211> LENGTH: 222
<212> TYPE: PRT
<213> ORGANISM: Artificial Sequence
<220> FEATURE:
<223> OTHER INFORMATION: Description of Artificial Sequence: Protein
sequence of mature Hercules bispecific antibody
light chain (LT-BS1)

<400> SEQUENCE: 8

```
Gln Leu Val Leu Thr Gln Ser Ser Val Ser Phe Ser Leu Gly Ala
  1               5                  10                  15

Ser Ala Lys Leu Thr Cys Thr Leu Ser Ser Gln His Ser Thr Tyr Thr
                 20                  25                  30

Ile Glu Trp Tyr Gln Gln Pro Leu Lys Pro Pro Lys Tyr Val Met
             35                  40                  45

Glu Leu Lys Lys Asp Gly Ser His Ser Thr Gly Asp Gly Ile Pro Asp
 50                  55                  60

Arg Phe Ser Gly Ser Ser Ser Gly Ala Asp Arg Tyr Leu Ser Ile Ser
 65                  70                  75                  80

Asn Ile Gln Pro Glu Asp Glu Ala Ile Tyr Ile Cys Gly Val Gly Asp
                 85                  90                  95

Thr Ile Lys Glu Gln Phe Val Tyr Val Phe Gly Gly Gly Thr Lys Val
                100                 105                 110

Glu Ile Lys Arg Thr Val Ala Ala Pro Ser Val Phe Ile Phe Pro Pro
            115                 120                 125

Ser Asp Glu Gln Leu Lys Ser Gly Thr Ala Ser Val Val Cys Leu Leu
        130                 135                 140

Asn Asn Phe Tyr Pro Arg Glu Ala Lys Val Gln Trp Lys Val Asp Asn
145                 150                 155                 160

Ala Leu Gln Ser Gly Asn Ser Gln Glu Ser Val Thr Glu Gln Asp Ser
```

-continued

```
                165                 170                 175
Lys Asp Ser Thr Tyr Ser Leu Ser Ser Thr Leu Thr Leu Ser Lys Ala
            180                 185                 190

Asp Tyr Glu Lys His Lys Val Tyr Ala Cys Glu Val Thr His Gln Gly
        195                 200                 205

Leu Ser Ser Pro Val Thr Lys Ser Phe Asn Arg Gly Glu Cys
    210                 215                 220
```